(12) United States Patent
Gephart et al.

(10) Patent No.: US 11,517,450 B2
(45) Date of Patent: Dec. 6, 2022

(54) INTERVERTEBRAL IMPLANT INSERTER TOOL

(71) Applicant: Pioneer Surgical Technology, Inc., Marquette, MI (US)

(72) Inventors: Matthew P. Gephart, Marquette, MI (US); Michael D. Kakuk, Skandia, MI (US); Emily Stilwell, Negaunee, MI (US); Jeffrey L. Trudeau, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 171 days.

(21) Appl. No.: 16/911,026

(22) Filed: Jun. 24, 2020

(65) Prior Publication Data

US 2020/0405502 A1     Dec. 31, 2020

Related U.S. Application Data

(60) Provisional application No. 62/867,487, filed on Jun. 27, 2019.

(51) Int. Cl.
*A61F 2/44* (2006.01)
*A61F 2/46* (2006.01)

(52) U.S. Cl.
CPC ..... *A61F 2/4611* (2013.01); *A61F 2002/4622* (2013.01); *A61F 2002/4629* (2013.01); *A61F 2002/4681* (2013.01)

(58) Field of Classification Search
CPC .......... A61F 2/4611; A61F 2/447; A61F 2/44; A61F 2/30771; A61F 2002/4622; A61F 2002/4629; A61F 2002/4681

USPC ........................ 623/17.11–17.16; 606/99–100
See application file for complete search history.

(56) References Cited

U.S. PATENT DOCUMENTS

| | | |
|---|---|---|
| 7,060,073 B2 | 6/2006 | Frey |
| 7,481,812 B2 | 1/2009 | Frey |
| 7,578,820 B2 | 8/2009 | Moore |
| 7,967,863 B2 | 6/2011 | Frey |
| 8,398,650 B1 | 3/2013 | Burgi |
| 8,808,307 B2 | 8/2014 | Robinson |

(Continued)

OTHER PUBLICATIONS

International Search Report and Written Opinion dated Nov. 17, 2020, in corresponding International Application No. PCT/US2020/039568 (14 pages).

(Continued)

*Primary Examiner* — Jessica Weiss
(74) *Attorney, Agent, or Firm* — Fitch, Even, Tabin & Flannery LLP

(57) ABSTRACT

In accordance with one aspect of disclosure, an inserter tool is provided for an elongate intervertebral implant. The inserter tool includes a body and a distal end portion of the body configured to be connected to the elongate intervertebral implant to orient the elongate intervertebral implant so that a longitudinal axis thereof extends in a predetermined direction. The inserter tool includes an offset member extending from the body. The offset member has an impact surface support portion spaced apart from the body and configured to position an impact surface in alignment with the implant longitudinal axis to permit the impact surface to receive an impact force directed in the predetermined direction.

28 Claims, 36 Drawing Sheets

(56) References Cited

U.S. PATENT DOCUMENTS

| | | |
|---|---|---|
| 8,828,082 B2 | 9/2014 | Puno |
| 9,345,586 B2 | 5/2016 | Hunt |
| 10,219,917 B2 | 3/2019 | Dewey |
| 2001/0027322 A1 | 10/2001 | Bowman |
| 2002/0019637 A1 | 2/2002 | Frey et al. |
| 2002/0165550 A1 | 11/2002 | Frey |
| 2003/0083747 A1* | 5/2003 | Winterbottom ....... A61F 2/4455 623/17.11 |
| 2004/0030346 A1 | 2/2004 | Frey |
| 2005/0049623 A1 | 3/2005 | Moore |
| 2006/0229627 A1 | 10/2006 | Hunt |
| 2006/0264968 A1 | 11/2006 | Frey |
| 2007/0093850 A1* | 4/2007 | Harris ................... H05B 47/11 606/99 |
| 2008/0306489 A1* | 12/2008 | Altarac ................. A61F 2/4611 606/99 |
| 2008/0306557 A1 | 12/2008 | Altarac |
| 2009/0248163 A1 | 10/2009 | King et al. |
| 2009/0270873 A1 | 10/2009 | Fabian |
| 2009/0312763 A1 | 12/2009 | McCormack |
| 2011/0009969 A1 | 1/2011 | Puno |
| 2011/0230970 A1 | 9/2011 | Lynn |
| 2012/0226357 A1 | 9/2012 | Varela |
| 2013/0282120 A1 | 10/2013 | Refai et al. |
| 2014/0018869 A1 | 1/2014 | Traynelis et al. |
| 2014/0172103 A1* | 6/2014 | O'Neil ................... A61F 2/4611 623/17.16 |
| 2014/0364917 A1* | 12/2014 | Sandstrom ............ A61F 2/4611 606/86 A |
| 2015/0045892 A1* | 2/2015 | Lynn .................... A61B 17/1671 623/17.16 |
| 2015/0297247 A1* | 10/2015 | Seex ..................... A61F 2/4684 606/85 |
| 2016/0058576 A1 | 3/2016 | Penenberg et al. |
| 2016/0228170 A1 | 8/2016 | Malcolmson |
| 2017/0100260 A1* | 4/2017 | Duffield ................ A61F 2/4611 623/17.16 |
| 2017/0119548 A1 | 5/2017 | Dewey |
| 2017/0156879 A1 | 6/2017 | Janowski |
| 2018/0140438 A1 | 5/2018 | Robinson |
| 2018/0161171 A1* | 6/2018 | Frasier .................. A61F 2/447 623/17.16 |
| 2018/0200077 A1* | 7/2018 | Knapp ................... A61F 2/4611 623/17.16 |
| 2019/0076266 A1 | 3/2019 | Trudeau |

OTHER PUBLICATIONS

Invitation to Pay Additional Fees mailed Sep. 4, 2020, in corresponding International Application No. PCT/US2020/039568 (2 pages).

* cited by examiner

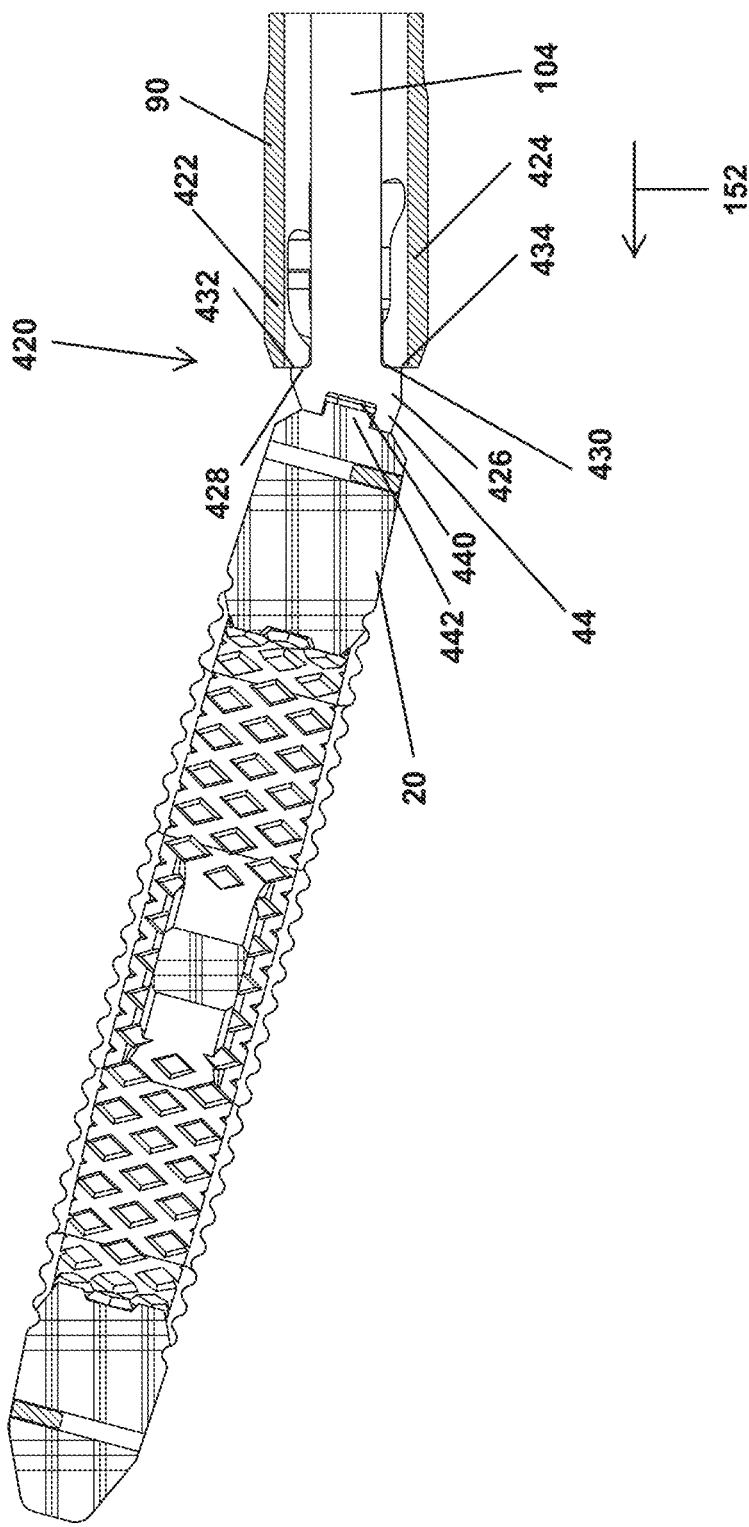

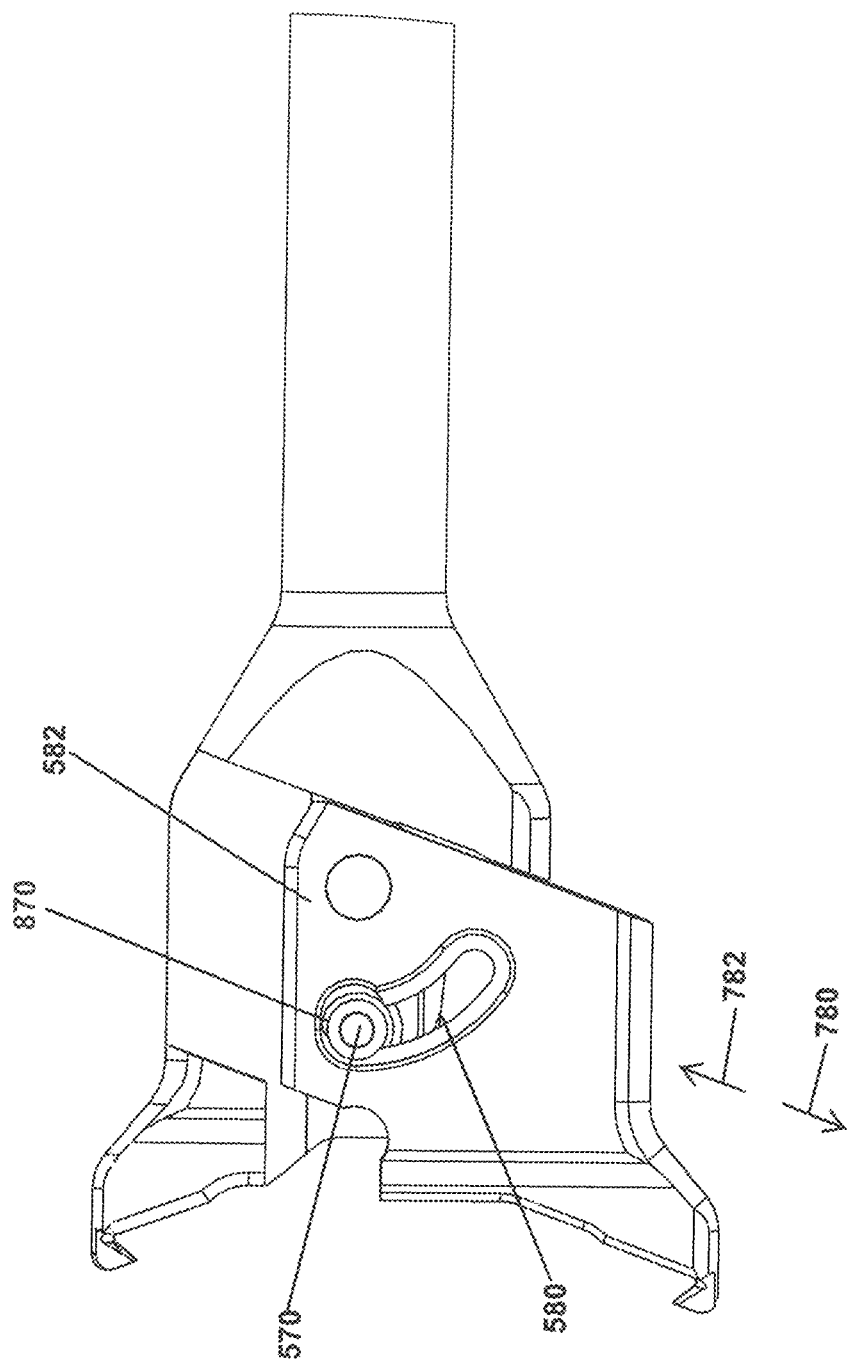

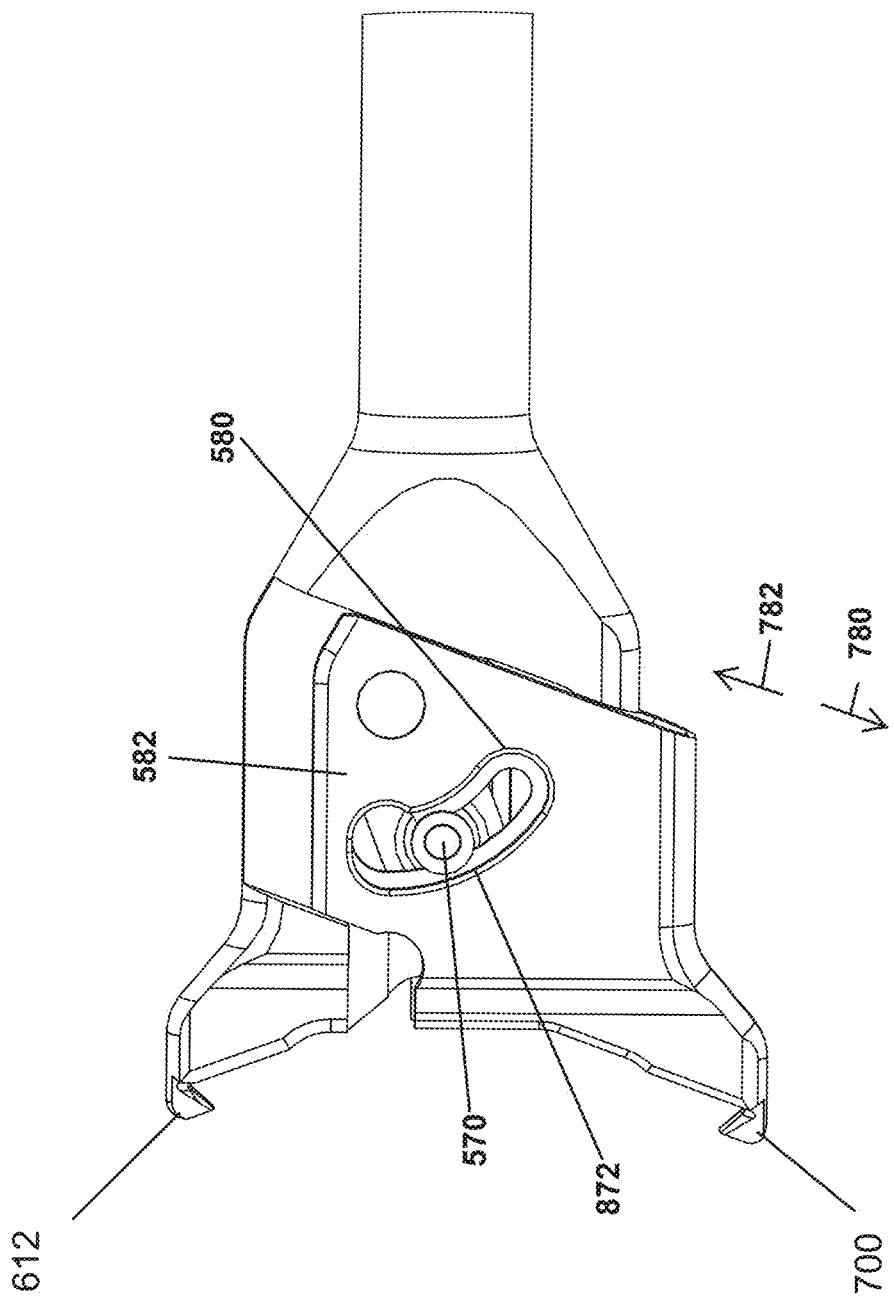

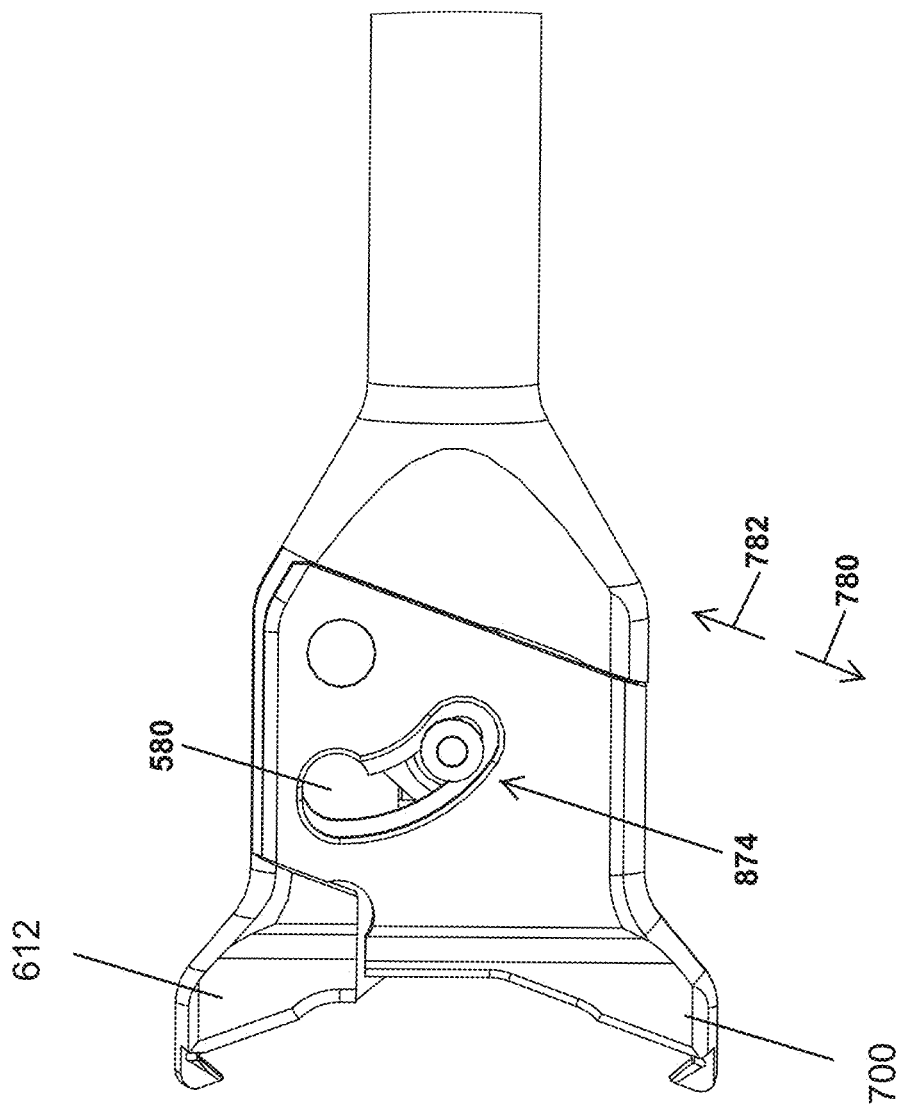

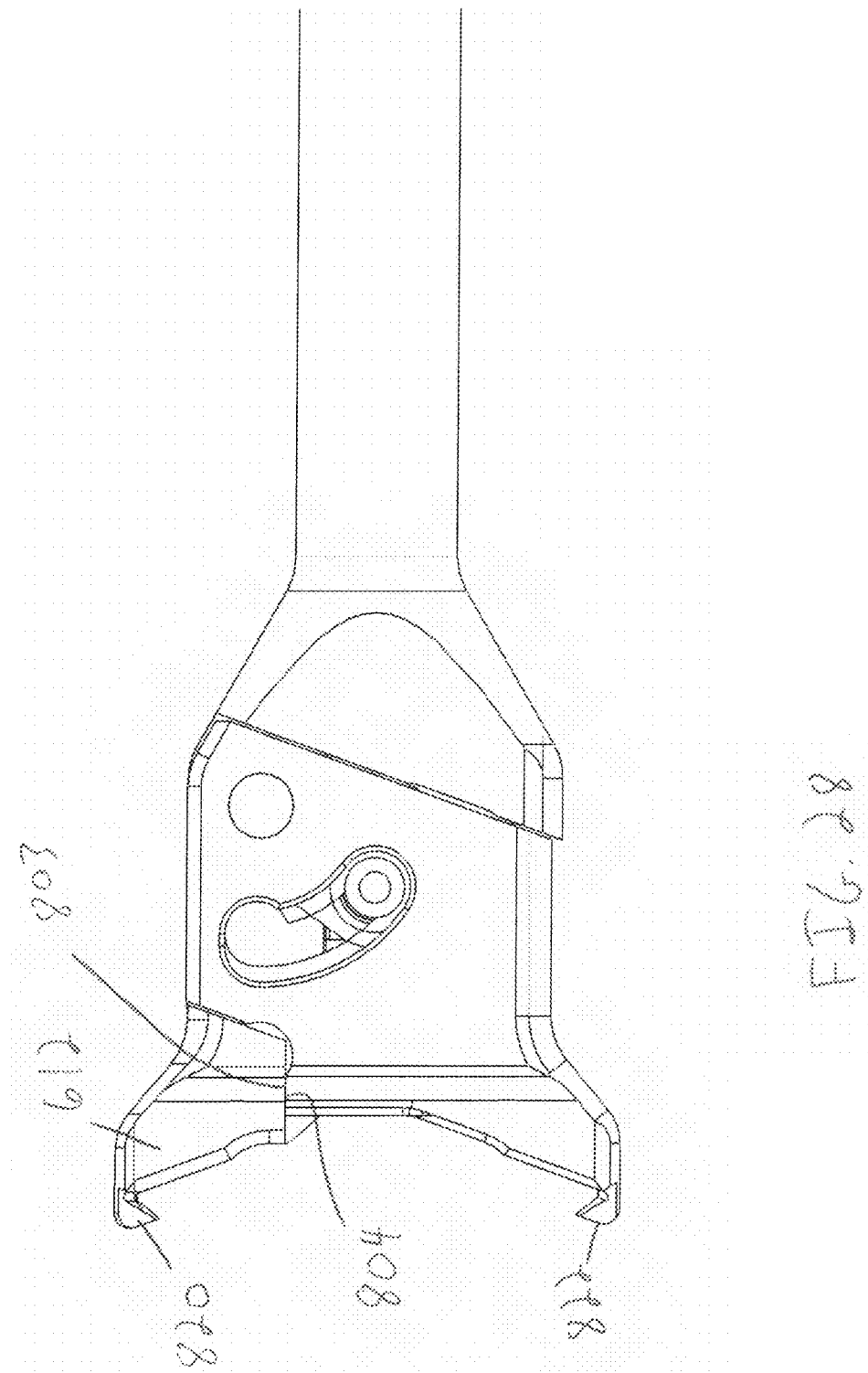

INTERVERTEBRAL IMPLANT INSERTER TOOL

CROSS-REFERENCE TO RELATED APPLICATION

This application claims the benefit of U.S. Provisional Patent Application No. 62/867,487, filed Jun. 27, 2019, which is hereby incorporated by reference in its entirety.

FIELD

This disclosure relates to surgical instruments and, more specifically, inserter tools for inserting implants into spaces between vertebrae.

BACKGROUND

Some spinal surgeries involve positioning an implant between vertebrae of a patient to stabilize the vertebrae. These types of surgeries may involve removing a portion of an annulus or the entirety of an annulus and a disc between the vertebrae and inserting one or more implants into the area previously occupied by the now-removed annulus or portion thereof. The implant may be advanced into the space between vertebrae using various approaches, such as anterior, posterior, or lateral approaches. Lateral or anterior approaches may be desirable in some situations because these approaches avoid the processes and lamina of the vertebrae.

However, utilizing a lateral approach for vertebrae in the lower lumbar region, such as the L4 and L5 vertebrae, is complicated by the patient's ilium or hip bone. In order to position an implant between the L4 and L5 vertebrae, the surgeon connects the implant to an inserter tool and advances the implant into a retracted incision formed in the patent along a path that avoids the ilium. This path is somewhat contorted, because the implant travels over the iliac crest and toward the spine.

Surgeons often select implants that have a height greater than the distance between the vertebrae so that the implant is compressed between the vertebrae when positioned in the intervertebral space. This compression may be utilized to improve the strength of the vertebral/implant construct and encourage bone growth. Due to the taller height of the implant, force is required to urge the vertebrae apart and advance the implant into the intervertebral space. A surgeon may apply the required force to the implant by tapping on a proximal end of the inserter tool using a hammer.

Some traditional intervertebral implants are made by machining a block of surgical-grade polyetheretherketone (PEEK) into the desired shape. These PEEK implants are rigid and readily resist impacts from a hammer. In contrast, some intervertebral implants are made using an additive manufacturing process that involves laser sintering PEEK or polyetherketoneketone (PEKK) particles into the desired implant shape. While these materials have a high compressive strength, the materials may have lower tensile properties.

Inserter tools are known that orient an implant at an oblique angle relative to a shaft of the inserter tool. The angle between the shaft and the implant permits the surgeon to direct the implant posteriorly into the intervertebral space while the shaft extends up and over the iliac crest. The inserter tool has a surface longitudinally aligned with the inserter tool shaft that may be struck with a hammer to drive the implant held by the inserter tool into an intervertebral space. When a surgeon strikes the inserter tool with a hammer, the inserter tool transfers the impact to the implant at the connection between the inserter tool and the implant. Traditional PEEK implants are sufficiently rigid to resist impacts typically applied by surgeons to advance the implants between vertebrae. However, some implants made using additive manufacturing that connect to conventional inserter tools are unable to withstand hammer impacts against the inserter tool. This issue is magnified by inserter tools having an oblique angle between the implant and the inserter tool shaft, which imparts a moment on the proximal end of the implant held by the inserter tool.

SUMMARY

In accordance to one aspect of the present disclosure, an inserter tool is provided for an elongate intervertebral implant. The inserter tool includes a body and a distal end portion of the body. The distal end portion is configured to be connected to the implant to orient the implant so that a longitudinal axis thereof extends in a predetermined direction. The inserter tool further includes an offset member extending from the body and an impact surface support portion of the offset member spaced apart from the body. The impact surface support portion is configured to position an impact surface in alignment with the implant longitudinal axis to permit the impact surface to receive an impact force directed in the predetermined direction. In this manner, the inserter tool permits an impact force to be transferred to the implant along the longitudinal axis thereof which minimizes the moment the inserter tool applies to a proximal end portion of the implant. By minimizing the moment, the proximal end portion of the implant is loaded in a compressive manner by the impact force rather than the proximal end portion being placed in tension and/or shear. This positions the implant, especially implants made using additive manufacturing techniques, to absorb the impact forces without disconnecting from the inserter tool.

In accordance with another aspect of the present disclosure, an inserter tool is provided for an intervertebral implant. The inserter tool includes an offset member, an elongate shaft having a proximal portion connected to the offset member, a distal portion opposite the proximal portion, and a longitudinal axis extending therebetween. The offset member has an impact surface spaced laterally from the longitudinal axis and on one lateral side thereof. The elongate shaft distal portion has a pair of arms with an unlocked configuration that permits the arms to be connected to the intervertebral implant and a locked configuration that secures the arms to the intervertebral implant. Each arm has a distal gripping portion extending obliquely to the longitudinal axis of the elongate shaft on an opposite lateral side of the longitudinal axis from the impact surface portion. The distal gripping portions of the arms are configured to orient the intervertebral implant so that the implant extends obliquely to the longitudinal axis of the elongate shaft on the opposite lateral side of the longitudinal axis. By positioning the impact surface support portion and the arm distal gripping portion on opposite lateral sides of the longitudinal axis, when an impact force is imparted to the impact surface support portion, the offset member and the elongate shaft may transfer the impact force around a patient's iliac crest, down into the pelvic area of the patient, and against the implant to advance the implant into the intervertebral space.

In accordance with another aspect of the current disclosure, an inserter tool is provided for an intervertebral implant and includes an elongate shaft comprising an outer sleeve and an inner shaft. The inserter tool includes a pair of arms associated with at least one of the outer sleeve and the inner shaft, the arms are resiliently biased apart and configured to engage the intervertebral implant. The inserter tool further includes a proximal actuator configured to shift the inner shaft and the outer sleeve relative to one another in a locking direction to urge the arms together against the resilient bias thereof and cause the arms to clamp a portion of the intervertebral implant therebetween. The actuator is further configured to shift the inner shaft and the outer sleeve relative to one another in an opposite, unlocking direction. The shifting of the inner shaft and outer sleeve relative to each other in the unlocking direction permits the resilient bias of the arms to separate the arms and release the implant portion. Upon the resilient bias of the arms being insufficient to separate the arms and release the implant portion, the outer sleeve and the inner shaft include cam surfaces configured to engage and separate the arms with shifting of the inner shaft and outer sleeve relative to each other in the unlocking direction.

BRIEF DESCRIPTION OF THE DRAWINGS

FIG. 11 is a cross-sectional view of the distal end portion of the inserter tool showing abutting surfaces of one of the arms and the sleeve that limit proximal movement of the inner shaft;

FIG. 12 is cross-sectional view of the arms of the inserter tool gripping an implant and showing laterally outer surfaces of the arms engaged with side walls of the outer sleeve such that the interference therebetween locks the arms in the closed configuration onto the implant;

FIGS. 25A, 25B, 26, 27, and 28 show the distal end of the inserter tool moving between an inner shaft removal configuration, a disassembled configuration, an open configuration, an implant-holding closed configuration, and a fully closed configuration;

DETAILED DESCRIPTION

Figure 1:
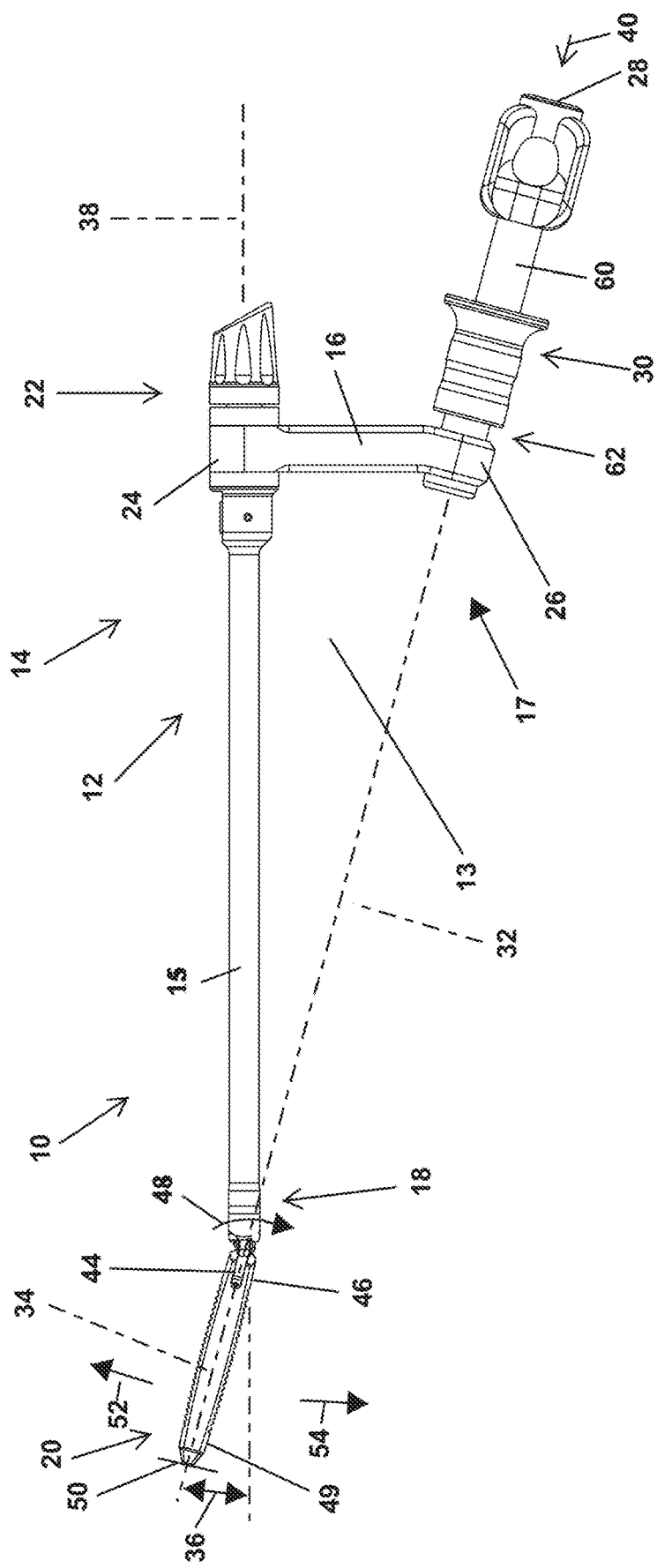
FIG. 1 is a side elevational view of an inserter tool having a distal end portion connected to an implant, a T-handle connected to a proximal end portion of the inserter tool, and an inserter tool axis that extends through an impact surface of the T-handle and is coaxial with a longitudinal axis of the implant.
Figure 2:
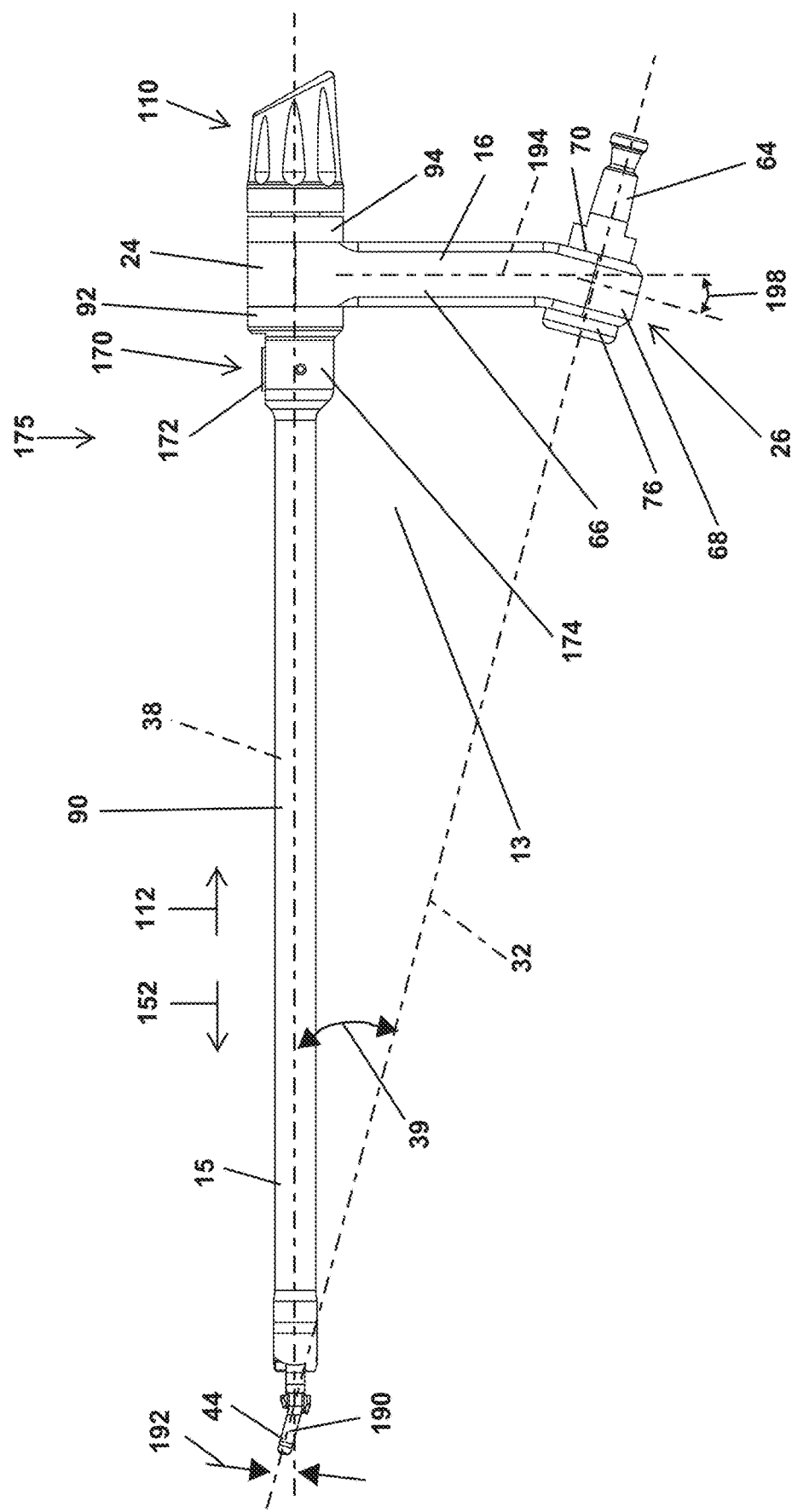
FIG. 2 is a side elevational view of the inserter tool of FIG. 1 with the T-handle and the implant removed and showing an angle between a longitudinal axis of a shaft of the inserter tool and the inserter tool axis.

With reference to FIGS. 1 and 2, an inserter tool 10 is provided that includes a body 12 having a housing 14 and an offset member, such as a handle 16. The body 12 may have a generally L-shape with a gap 13 that may receive an ilium of a patient so that the handle 16 is on a laterally outer side of the ilium while the housing 12 extends into the patient inferiorly along the opposite, inner side of the ilium. The body 12 may thereby positioned to extend around the iliac crest of a patient. The inserter tool 10 has a distal end portion 18 configured to be releasably connected to an implant 20. The inserter tool 10 includes a shaft 15 sized to position a proximal end portion 17 of the inserter tool 10 outside of a patient while the distal end portion 18 is positioned adjacent vertebral bones of the patient. The inserter tool 10 has an actuator 22 that may be operated to shift the distal end portion 18 from a release or open configuration that permits the distal end portion 18 to be connected to the implant 20 to a locked or closed configuration that secures the implant 20 to the distal end portion 18. In one embodiment, the distal end portion 18 includes arms 44 configured to clamp the implant 20 therebetween with the distal end portion 18 in the open configuration thereof.

The handle 16 has a base or receiving portion 24 mounted to the housing 14 and a free end portion, such as an impact surface support portion 26, spaced from the housing 14. The impact surface support portion 26 positions an impact surface, such as a surface 28 of a force imparting tool 30, to be intersected by an inserter axis 32. The inserter axis 32 operates as a virtual load path along which impacts against the impact surface 28 are transferred to the implant 20. The inserter axis 32 is coaxially aligned with a central, longitudinal axis 34 of the implant 20. The distal end portion 18 positions the implant 20 so that the implant axis 34 extends at an angle 36 relative to a longitudinal axis 38 of the housing 14 (see FIG. 2). The angle 36 may be in the range of, for example, approximately 1 degree to approximately 40 degrees, such as approximately 5 degrees to approximately 20 degrees, such as approximately 15 degrees.

The handle 16 and housing 14 are rigidly joined so that an impact force in direction 40 against the impact surface 28 is transmitted through the handle 16, the housing 14, and to the arms 44 gripping the implant 20. Because the impact force direction 40 is aligned with the inserter axis 32 and the implant longitudinal axis 34 extending therealong, the impact force 40 is imparted to the implant 20 without a lateral offset. Because there is no lateral offset, the impact force in direction 40 does not generate a bending moment about a proximal end portion 46 of the implant 20, such as in direction 48. Rather, the impact force in direction 40 is translated into the implant 20 to drive a distal end portion 49 linearly into an intervertebral space. The linear application of force to the implant 20 in direction 40 against the impact surface 28 applies a compressive load to the implant 20, rather than a bending or shear load. The implant 20 may be made using an additive manufacturing process and may be more brittle than a conventional implant made by machining the implant from a block of PEEK. The inserter tool 10 transfers loading in a compressive manner to the implant 20, which the implant 20 is better able to handle, than bending which may be imparted by a conventional inserter tool. Further, the impact force in direction 40 may drive the distal end portion 49 against a surface 50, such as surfaces of vertebrae on opposite sides of an intervertebral space, in a direction normal to the surface 50. This straightforward or longitudinal application of force resists shifting of the distal end portion 49 in directions 52, 54 as impacts are directed in directions 40 against the impact surface 28. By applying force in the longitudinal direction, the surgeon has improved control over driving the implant 20 into an intervertebral space with minimal shifting in directions 52, 54.

Regarding FIG. 2, the longitudinal axis 38 of the housing 14 extends at an angle 39 relative to the inserter tool axis 32. Further, the arms 44 include gripping portions 190 that extend obliquely, such as at an angle 192, relative to the longitudinal axis 38. The angle 192 may be in the range of, for example, approximately 1 degree to approximately 40 degrees, such as approximately 5 degrees to approximately 20 degrees, such as 15 degrees. The handle 16 extends along a support axis 194 and may be elongated along the axis 194. The loop portion 68 of the handle 16 positions the impact surface support portion 26 to extend at an angle 198 relative to the axis 194. In one embodiment, the angle 198 is the same as the angle 192. The gripping portions 190 position the implant 20 obliquely relative to the shaft 15 on an opposite side of the axis 38 from the impact surface 28. By positioning the implant 20 and impact surface 28 on opposite sides of the longitudinal axis 38, the handle 16 and the shaft 15 permit a surgeon to transfer an impact force up and around a patient's iliac crest, down into the pelvic area of the patient, and against the implant 20 to advance the implant into an intervertebral space.

With reference to FIGS. 1 and 2, the force imparting tool 30 may be a T-handle 60 that is connected to the handle 16 via a releasable connection 62. The force imparting tool 30 may take other forms, such as a slap hammer. The releasable connection 62 may include, for example, a Hudson connector. In one embodiment, the releasable connection 62 includes a male connector 64 that is mounted to the handle 16. Regarding FIGS. 2 and 3, the handle 16 includes an elongate gripping portion 66 and a loop portion 68 extending about a through opening 70. The male connector 64 includes a body 72, a connector fastener 74, and a connector member 76 that are secured to the handle 16. The connector member 76 may include a projection 78 having a non-circular shape, such as a square. The projection 78 mates with the opening 70 of the handle 16, which may be non-circular, such as a square. The body 72 of the male connector 64 also includes a projection 82 that may have a non-circular cross section. In one approach, the projections 78, 82 and opening 70 have a mating square arrangement that resists turning of the connector 64 once installed. The connector fastener 74 has a threaded shank 75 that engages a threaded bore of the body 72. The connector fastener 74 rigidly clamps the loop portion 68 of the handle 16 between the connector member 76 and the body 72 of the male connector 64. The rigid connection between the male connectors 64 and the handle 16 transfers impacts from the impact surface 28 to the handle 16.

Figure 3:
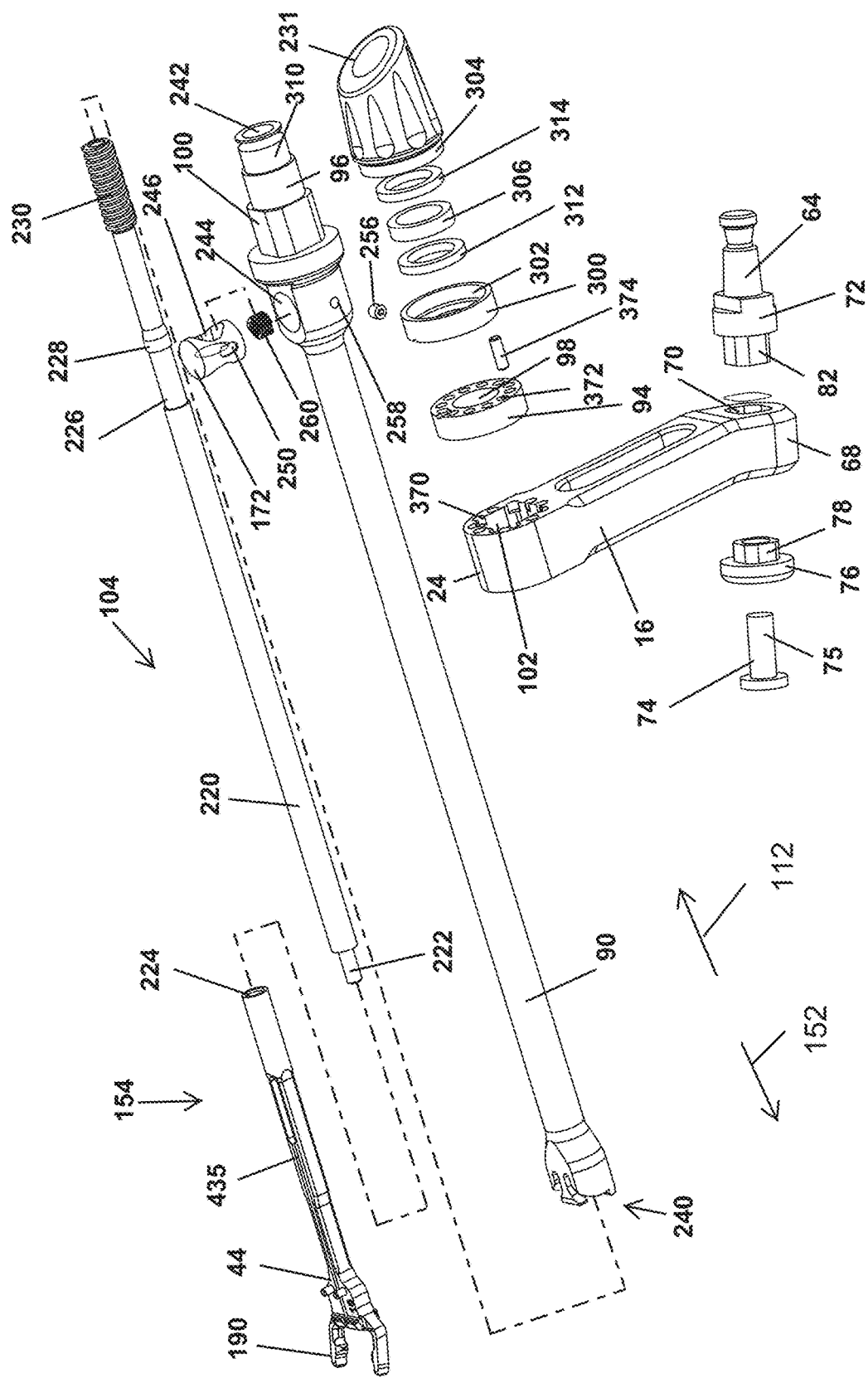
FIG. 3 is an exploded view of the inserter tool of FIG. 2 showing an inner shaft, an outer sleeve, a handle, and a knob assembly of the inserter tool.

With reference to FIGS. 2 and 3, the housing 14 includes an outer sleeve 90 having a flange 92 and a locking member, such as a nut 94. The outer sleeve 90 has a locking portion 96 configured to engage the nut 94. In one embodiment, the locking portion 96 has radially outer threads that engage radially inner threads 98 of the nut 94. The outer sleeve 90 further includes a mounting portion 100 that extends through a through opening 102 of the handle 16. During assembly of the inserter tool 10, the nut 94 is threadingly engaged with the locking portion 96 of the outer sleeve 90 to clamp the receiving portion 24 of the handle 16 between the flange 92 and the nut 94. The inserter tool 10 further includes a locking member, such as a pin 374, that fixes the nut 94 against loosening movement relative to the outer sleeve 90. In one embodiment, the pin 374 extends through one of the holes 372 of the nut 94 and into a pocket 370 of the handle 16. The components of the inserter tool 10 may be made from metallic and/or plastic materials that are sufficiently strong to withstand loading applied during an implant installation. The components may also be made of materials that may be cleaned using an autoclave or gamma radiation, as some examples. For example, the sleeve 90 and nut 94 may be made of a stainless steel and the pin 374 may be made of a hardened stainless steel to resist the shear loading applied to the pin 374 by the sleeve 90 and the nut 94.

Figure 4:
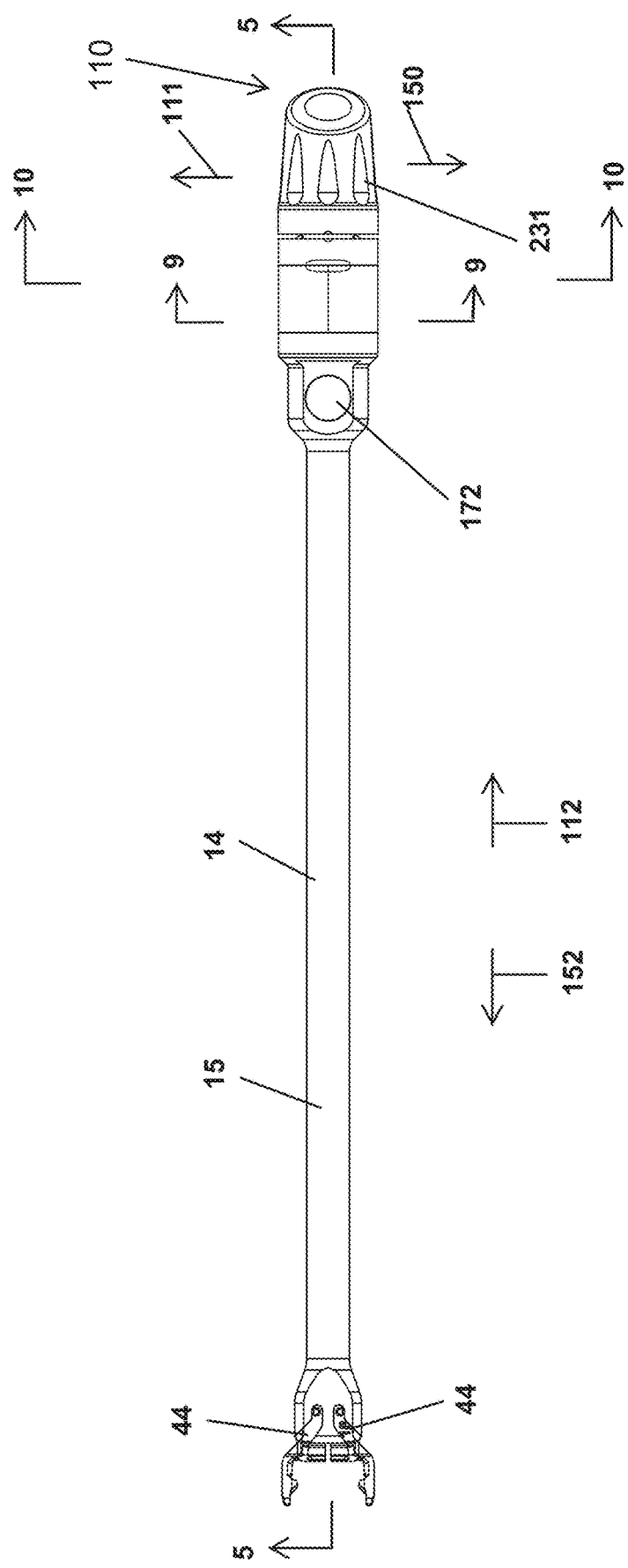
FIG. 4 is a top plan view of the inserter tool of FIG. 2 showing distal arms of the inner shaft in an open configuration.
Figure 6:
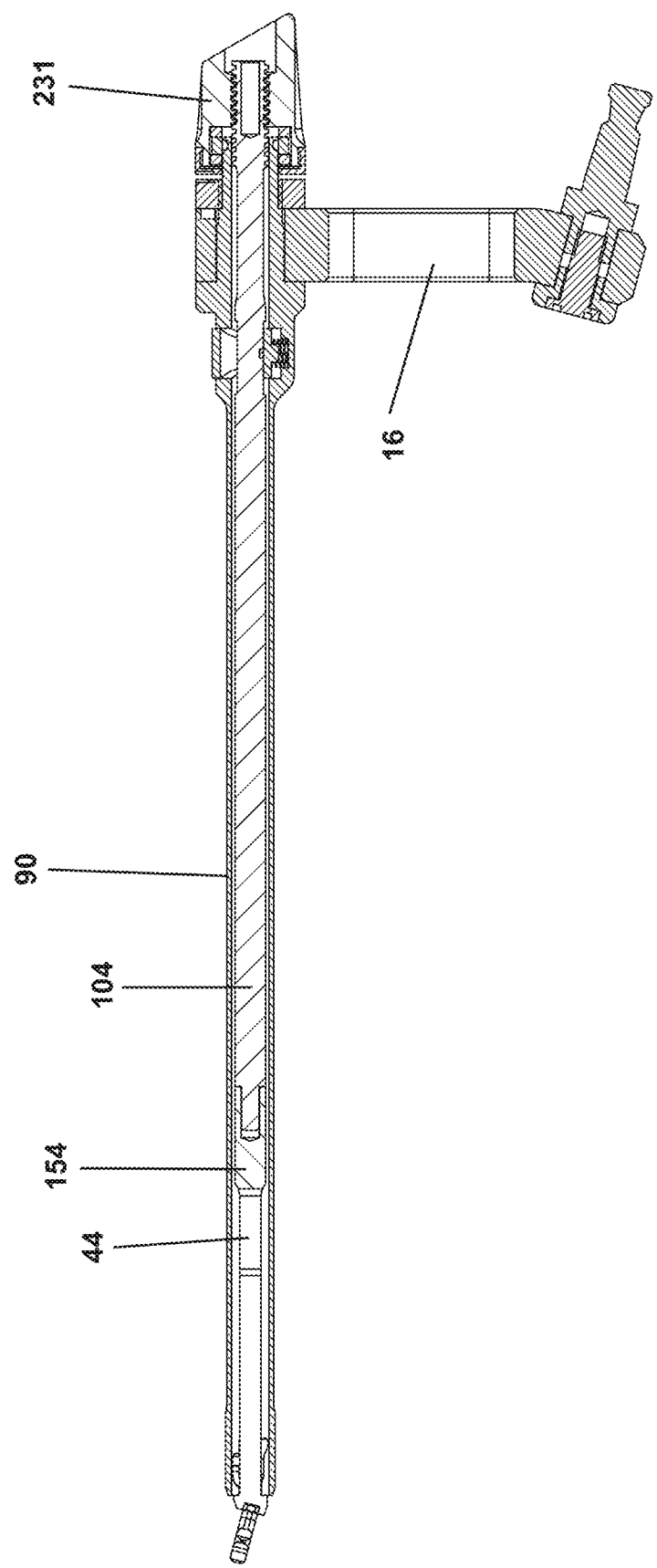
FIG. 6 is a cross-sectional view similar to FIG. 5 showing the knob assembly having been turned to shift the inner shaft proximally to a closed position and cause the outer sleeve to cam together the arms.

Regarding FIGS. 3 and 4, the body 12 (see FIG. 1) further includes an inner shaft 104 that is slidably received in the outer sleeve 90. To reconfigure the distal end portion 18 from an open configuration to a closed configuration or vice versa, the actuator 22 in one embodiment includes a knob assembly 110 having a knob 231 that is turned in a direction 111 to draw the inner shaft 104 in proximal direction 112 and reconfigures the distal end portion 18 to a closed configuration as shown in FIG. 6. The movement of the inner shaft 104 in direction 112 causes cam surfaces 114, 116 (see FIG. 12) of the arms 44 to cammingly engage surfaces 118, 120 of the sleeve 90, which shifts the arms 44 together and clamps a proximal portion 122 of the implant 20 therebetween. Once the arms 44 have shifted proximally sufficiently far so that lands 130, 132 are abutting interference surfaces 134, 136, the land surfaces 130, 132 have a distance 138 therebetween that is larger than a distance between the interference surfaces 134, 136. This creates an interference fit between the arms 44 and the sleeve 90 and fixes the arms 44 at a longitudinal position relative to the sleeve 90 and locks the arms 44 onto the implant 20. In another embodiment, the outer sleeve 90 may shift along the inner shaft 104.

Figure 5:
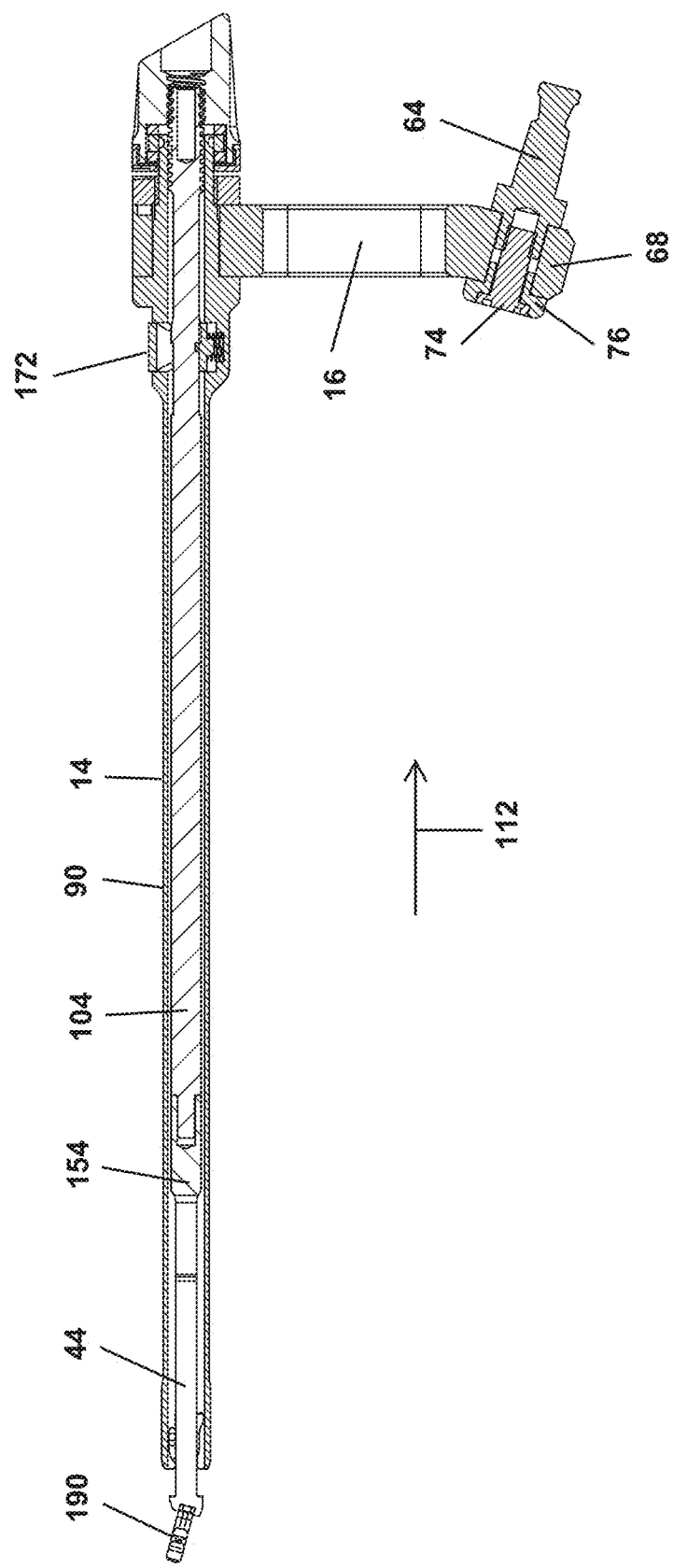
FIG. 5 is a cross-sectional view taken across line 5-5 in FIG. 4 showing the inner shaft in an open position such that the arms may receive an implant.

With reference to FIG. 4, turning of the knob 231 in direction 150 shifts the inner shaft 104 in distal direction 152 and shifts the distal end portion 18 to an open configuration as shown in FIG. 5. The inner shaft 104 includes a resilient fork portion 154 (see FIG. 3) which includes the arms 44. The resiliency of the fork portion 154 urges the arms 44 apart to the open configuration as the lands 130, 132 are shifted distally in direction 152 away from the interfering position with the interference positions 134, 136 of the sleeve 90. In some instances, the resiliency of the fork portion 154 is sufficient to disengage protrusions 160 (see FIG. 12) of the arms 44 from pockets 162 of the implant 20. In these situations, the inserter tool 10 may then be removed from the surgical site.

With reference to FIGS. 2 and 4, the inserter tool 10 may be readily disassembled for cleaning. For example, the inserter tool 10 may have a release mechanism 170 that selectively limits how far the inner shaft 140 may shift in direction 152. In one embodiment, the release mechanism 170 includes a detent member, such as a button 172, received at least partially in a release compartment 174 of the housing 14. As discussed in greater detail below with respect to FIGS. 7 and 8, the button 172 may be pressed in direction 175 to shift the button 172 from a blocking position where the button 172 limits longitudinal movement of the inner shaft 104 in distal direction 152 to a clearance position where the button 172 permits shifting of the inner shaft 104 in the distal direction 152 to permit removal of the inner shaft 104 from the sleeve 90.

With reference to FIG. 3, the inner shaft 104 may include the resilient fork portion 154 and a drive portion 220. The drive portion 220 may have a pin 222 that is received in a socket 224 of the resilient fork portion 154. The drive portion 220 and resilient fork portion 154 may be welded together and/or joined using a fastener. In another embodiment, the inner shaft 104 has a unitary, one-piece construction including the resilient fork portion 154 and the drive portion 220.

The drive portion 220 includes a reduced diameter portion 226, a shoulder 228, and a threaded portion 230. The knob 231 of the knob assembly 110 includes a drive portion 232 (see FIG. 7) that cooperates with the inner shaft 104 to drive the inner shaft 104 in proximal direction 112 or distal direction 152 with operation of the knob 231. In one embodiment, the knob 231 includes a bore 234, which may be a blind bore or a through bore, with threads 236 that engage threads 238 of the threaded portion 230 of the inner shaft 104. The threads 236, 238 may be ACME threads. The engaged ACME threads provide a mechanical advantage to a surgeon as the surgeon turns the knob 231 to shift the inner shaft 104 in directions 112, 152. In some embodiments, ACME threads are selected to permit farther shifting of the inner shaft 104 in directions 112, 152 for a given turn of the knob 231 than would be obtained using standard machine threads.

Figure 7:
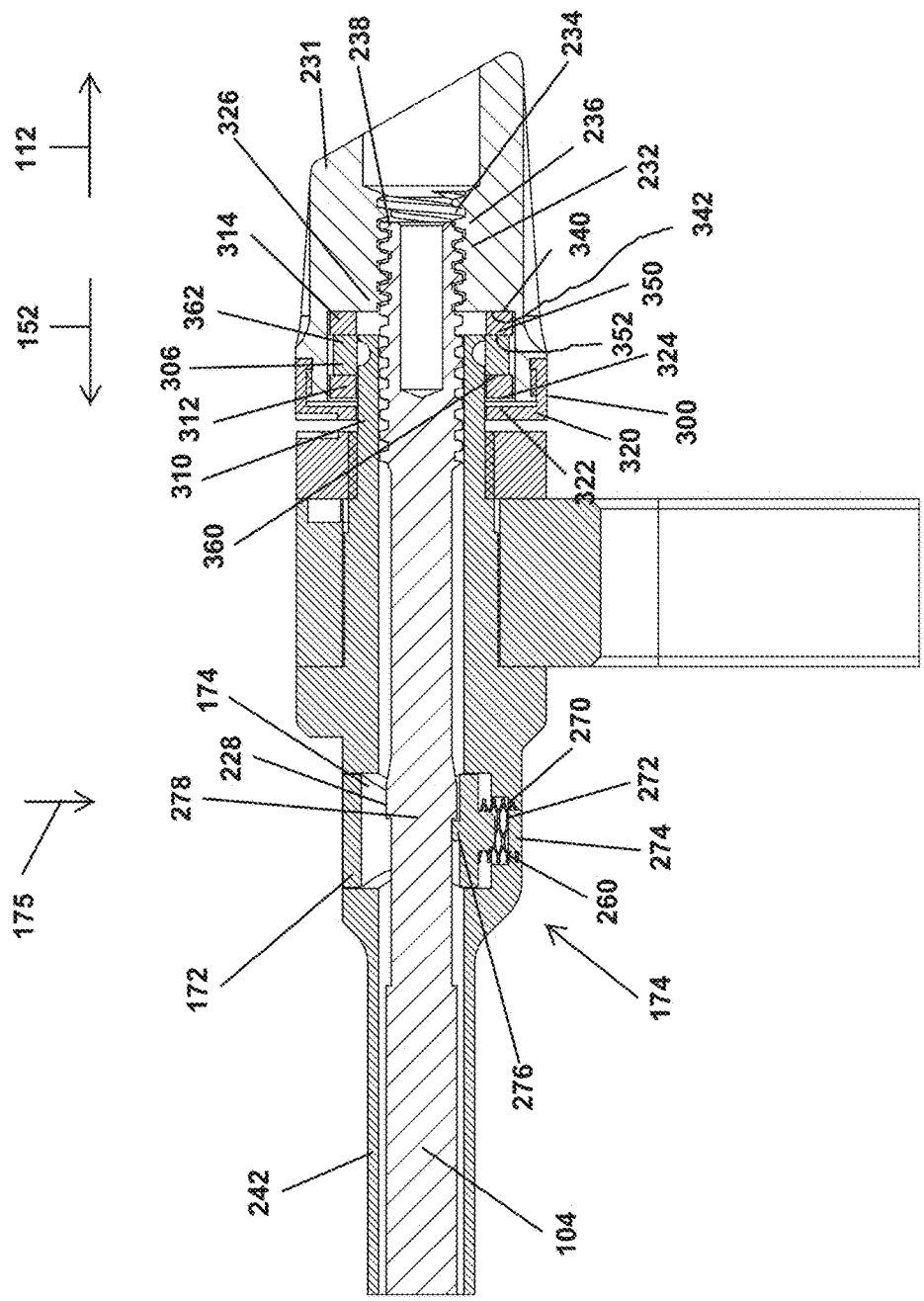
FIG. 7 is an enlarged view of a portion of FIG. 5 showing a release button of the inserter tool in a blocking position that resists removal of the inner shaft in a distal direction from within the outer sleeve.
Figure 8:
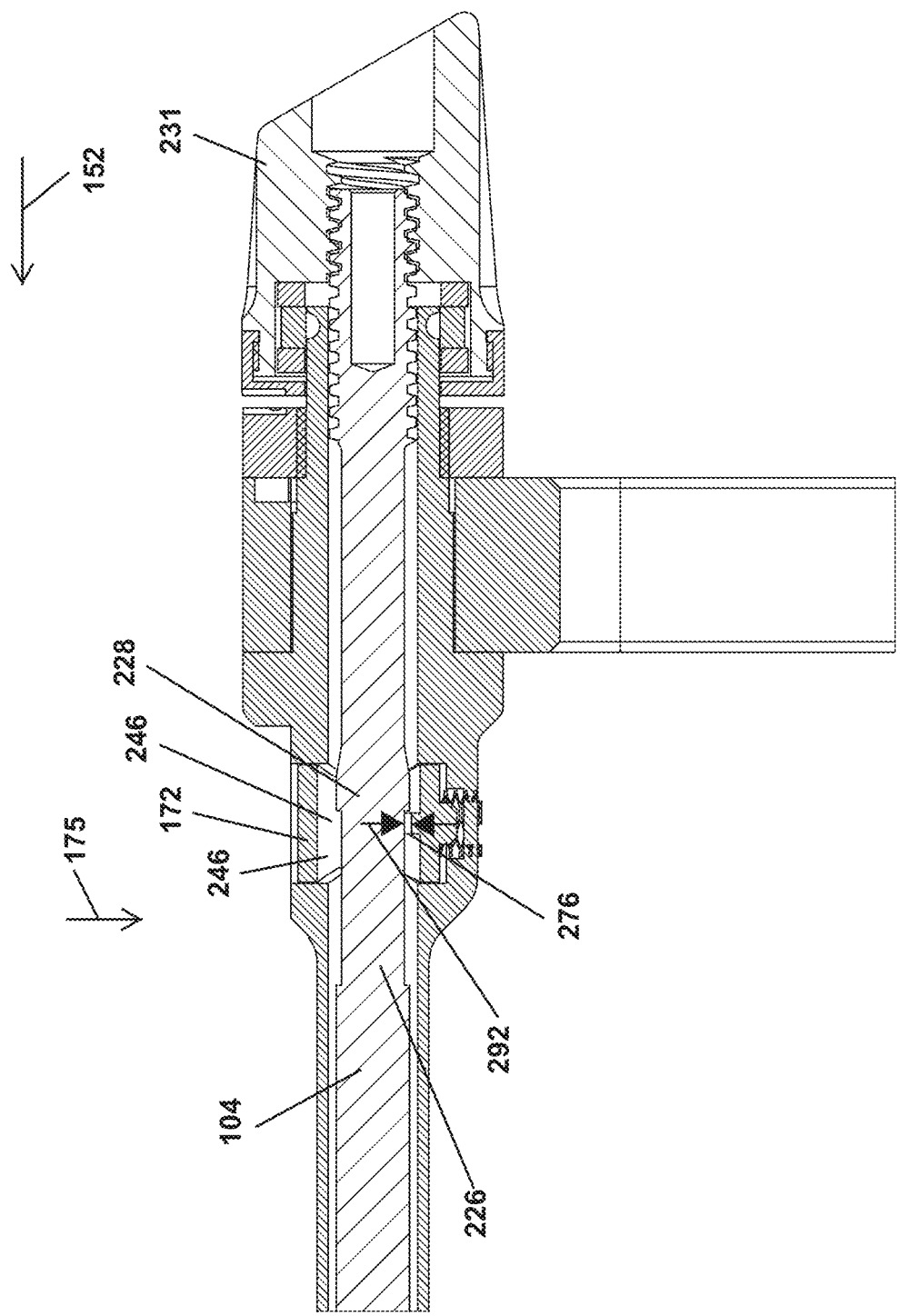
FIG. 8 is a view similar to FIG. 7 showing the release button shifted to a clearance position wherein the release button permits the inner shaft to be shifted distally out of the outer sleeve for disassembly.

Regarding FIGS. 7 and 8, to assemble the inner shaft 104 and the outer sleeve 90, the button 172 is pressed radially inward in direction 175 from the blocking position of FIG. 7 into the release position of FIG. 8. Next, the threaded portion 230 of the inner shaft 104 is advanced in the proximal direction 112 into a throughbore 242 of the sleeve 90. The threaded portion 230 of the inner shaft 104 is advanced in proximal direction 112 through a through opening 246 of the button 172 until the threaded portion 230 extends proximally outward from a support portion 310 (see FIGS. 3 and 7) of the sleeve 90 and the reduced diameter portion 226 of the inner shaft 104 is positioned in the button through opening 246 (see FIG. 8). With the threaded portion 230 of the inner shaft 104 extending proximally of the sleeve support portion 310, the support portion 310 and threaded portion 230 may be advanced through the through opening 102 (see FIG. 3) of the handle 16 and the nut 94 threaded onto the locking portion 96 of the sleeve 90. As discussed in greater detail below, the nut 94 is tightened to clamp the handle 16 between the nut 94 and the flange 92 of the sleeve 90 and fixed in position by the pin 374.

Regarding FIG. 3, the button 172 includes an elongated slot 250 that receives a portion of an alignment member, such as a dog point screw 256, that extends through an opening 258 of the sleeve 90. The release mechanism 170 includes a biasing member, such as a spring 260, which may be a wave spring, that is received in the opening 244 and biases the button 172 toward the interference or blocking position thereof.

With reference to FIG. 7, the release compartment 174 includes a spring recess 270 having a spring seat 272 that supports the lower end of the spring 260. The button 172 includes a locator pin 274 that extends and keeps the spring 260 in position between the button 172 and the seat 272. The button 172 has a stop, such as a projection 276, that is axially aligned with a radially extending surface 278 of the shoulder 228. With the button 172 in the blocking position, the user turning the knob 231 to shift the inner shaft 104 in distal direction 152 would be limited by the contact between the projection 276 of the button 172 and the surface 278 of the inner shaft shoulder 228. In this manner, the button 172 inhibits the user from unintentionally disassembling the inner shaft 104 when the user is intending to shift the inner shaft 104 distally in direction 152 to disengage the arms 44 from the implant 20.

With reference to FIG. 8, the user may press the button 172 in direction 175 to shift the button 172 to the clearance position thereof such that there is a radial clearance distance 292 between the shoulder 228 and the projection 276. With the projection 276 in clearance with the shoulder 228, the user may turn the knob 231 and use the threaded engagement between the knob 231 and the inner shaft 104 to drive the inner shaft 104 distally in direction 152 until the inner shaft 104 is disconnected from the knob 231. At this point, the user may withdraw the inner shaft 104 from the sleeve 90.

With reference to FIG. 3, the knob assembly 110 is rotatably captured on the sleeve 90 so that the knob 231 may be turned relative to the sleeve 90 to shift the inner shaft 104 in the proximal or distal directions 112, 152 via the engagement between the threads 236, 238 of the inner shaft 104 and the knob 231. In one embodiment, the knob assembly 110 includes a knob cap 300 having threads 302 that are engaged with threads 304 of the knob 231. The knob cap 300 and knob 231 are connected together around a washer 306 that is welded to the support portion 310 of the sleeve 90. In another embodiment, the washer 306 is connected to the support portion 310 via a pair of pins extending like chords through holes in the washer 306 and received in an annular groove in the support portion 310. The knob assembly 110 includes bushings 312, 314 that contact the washer 306 and permit turning of the knob 231 and knob cap 300 while reducing friction between the knob cap 300 and the knob 231. The bushings 312, 314 may be made of a plastic, such as rayon, and the washer 306, knob 231, and knob cap 300 may be made of one or more metallic materials, such as stainless steel and/or titanium.

More specifically and with reference to FIG. 7, the knob cap 300 has a collar 320 with an annular surface 322 facing a distal surface 324 of the bushing 312. Likewise, the knob 231 includes an annular wall 326 extending about the bore 234 and having a distal annular surface 340 facing a proximal surface 342 of the bushing 314. When the knob 231 is turned in direction 111 (see FIG. 4), the surface 340 of the knob 231 is pressed in distal direction 152 against the surface 342 of the bushing 314 which, in turn, presses a distal surface 350 of the bushing 314 against a proximal surface 352 of the washer 306. The engagement between threads 236, 238 of the inner shaft 104 and the knob 231 thereby transfers turning of the knob cap 300 in direction 111 into linear movement of the inner shaft 104 in the proximal direction 112.

Conversely, when the knob 231 is turned in direction 150 (see FIG. 4), a surface 322 of the knob cap collar 320 presses in proximal direction 112 against the distal surface 324 of the bushing 312. This presses a proximal surface 360 of the bushing 312 against a distal surface 362 of the washer 306. The threaded engagement between the knob 231 and the inner shaft 104 thereby transfers turning of the knob cap 300 in direction 150 into linear movement of the inner shaft 104 in the distal direction 152. In this way, the bushings 312, 314 reduce friction and make it easier for a surgeon to turn the knob 231 and shift the arms 44 between open and closed positions.

With reference to FIG. 3, the handle 16, nut 94 and sleeve 90 are configured to provide rigidity against rotation and bending of the handle 16 relative to the sleeve 90. More specifically, the receiving portion 24 of the handle 16 includes one or more pockets 370 about the through opening 102. The pockets 370 may be in communication with the through opening 102. The nut 94 includes one or more holes 372 about the opening 98. The pin 374 is advanced through one of the holes 372 and into one of the pockets 370 once the nut 94 has been tightened down to lock the relative rotation positions of the sleeve 90 and the nut 94. The pin 374 may be welded to the nut 94 and/or the handle 16 to fix the pin 374 in position.

Figure 10:
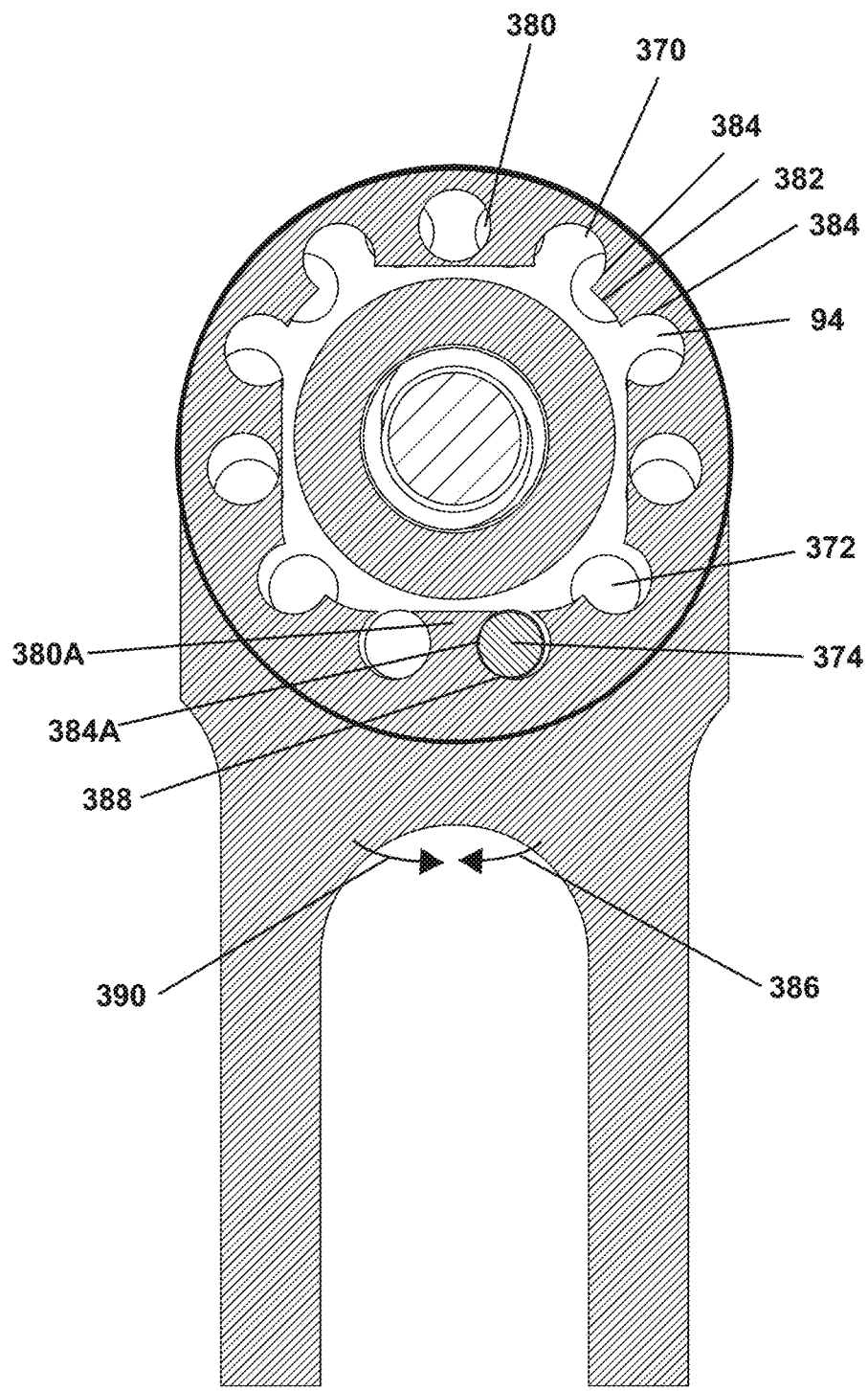
FIG. 10 is a cross-sectional view taken across line 10-10 in FIG. 4 showing a locking nut of the housing held in position by a pin that extends through an opening of the locking nut and into a pocket of the handle.
Figure 1D:
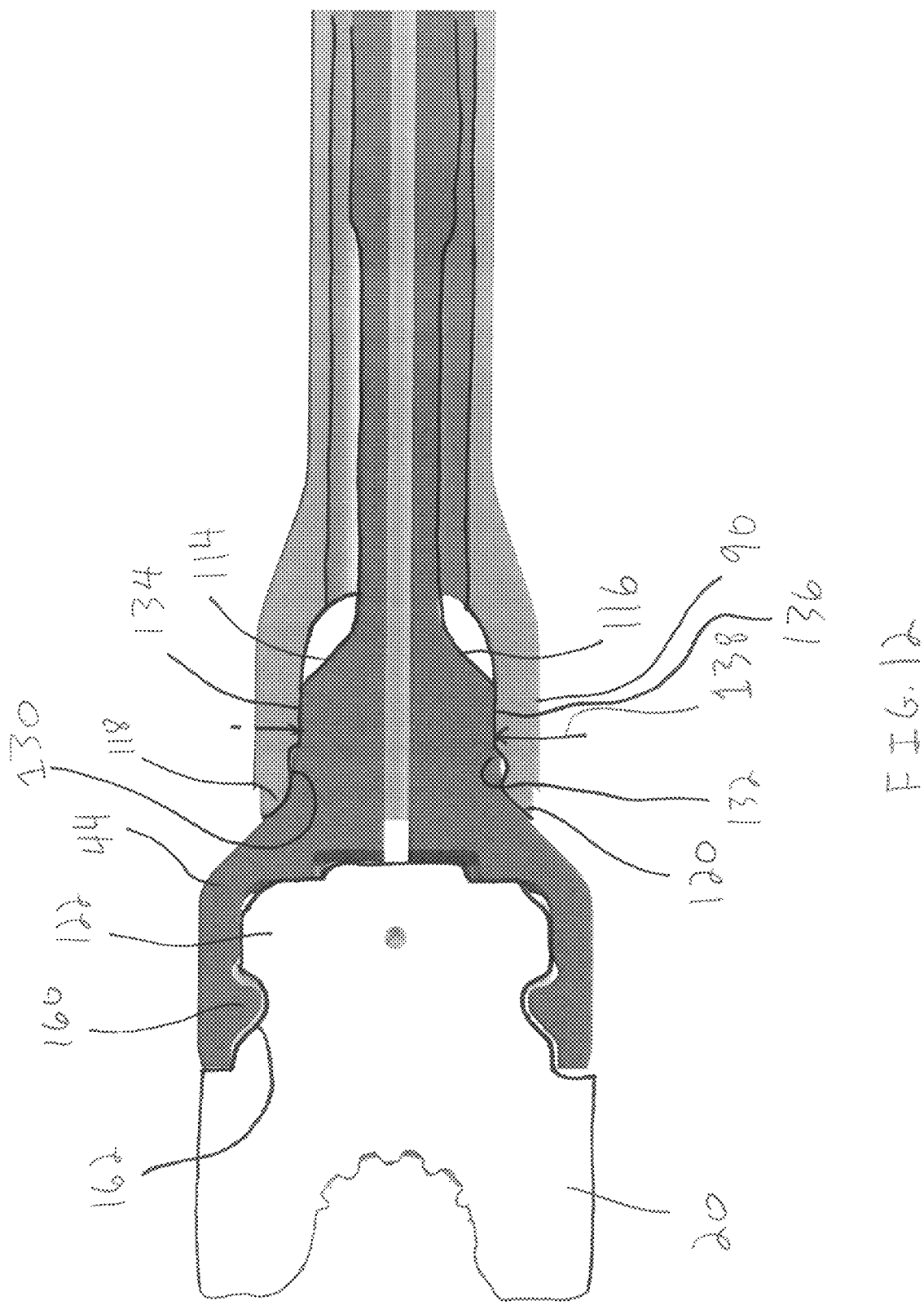

With reference to FIG. 10, the nut 94 is configured so that there is only one aligned hole 372 of the nut 94 and one pocket 370 of the handle 16 at a given rotary position of the nut 94. As the nut 94 is tightened, the aligned hole 372 and pocket 370 will change to another hole 372 and pocket 370 and the remaining holes 372 will be mis-aligned. The sequential alignment of only one hole 372 at a time with one pocket 370 permits a manufacturer to specify that the pin 374 should be inserted through a particular hole 372 and into the aligned pocket 370 and, if the pin 374 is so inserted, the torque experienced by the nut 94 will be the torque dictated by the position of the nut 94. This permits a manufacturer to ensure the nut 94 has been torqued down to a predetermined torque. In other words, a user would be unable to insert the pin 374 through the designated hole 372 and into the associated pocket 370 until the nut 94 has been turned sufficiently far to align the hole 372 with the associated pocket 370.

Each pocket 370 includes a pair of walls 380, 382 with side surfaces 384 that may be curved to complement an outer surface 388 of the pin 374. As shown in FIG. 10, the holes 372 are slightly mis-aligned so that the nut 94 must be slightly over-tightened in order to fully align one of the holes 372 with one of the pockets 370 and permit the pin 374 to be inserted through the aligned hole 372 and pocket 370. Once the pin 374 has been inserted, the nut 94 needs to turn in direction 386 to loosen from the sleeve 90. The outer surface 388 of the pin 374 is engaged with a side surface 384A of a wall 380A due to the over-tightening of the nut 94. This engagement places the pin 374 in shear. The pin 374 is selected from a material, such as stainless steel, sufficient to resist the shear loading and inhibit relative turning of the nut 94 in direction 386. In this manner, the wall 380A applies a reaction force in direction 390 that resists movement of the pin 374 in direction 386 and the nut 94 and loosening of the nut 94. The nut 94 thereby securely maintains flange 92 of the sleeve 90 and the nut 94 in a clamping arrangement about the receiving portion 24 of the handle 16.

Figure 9:
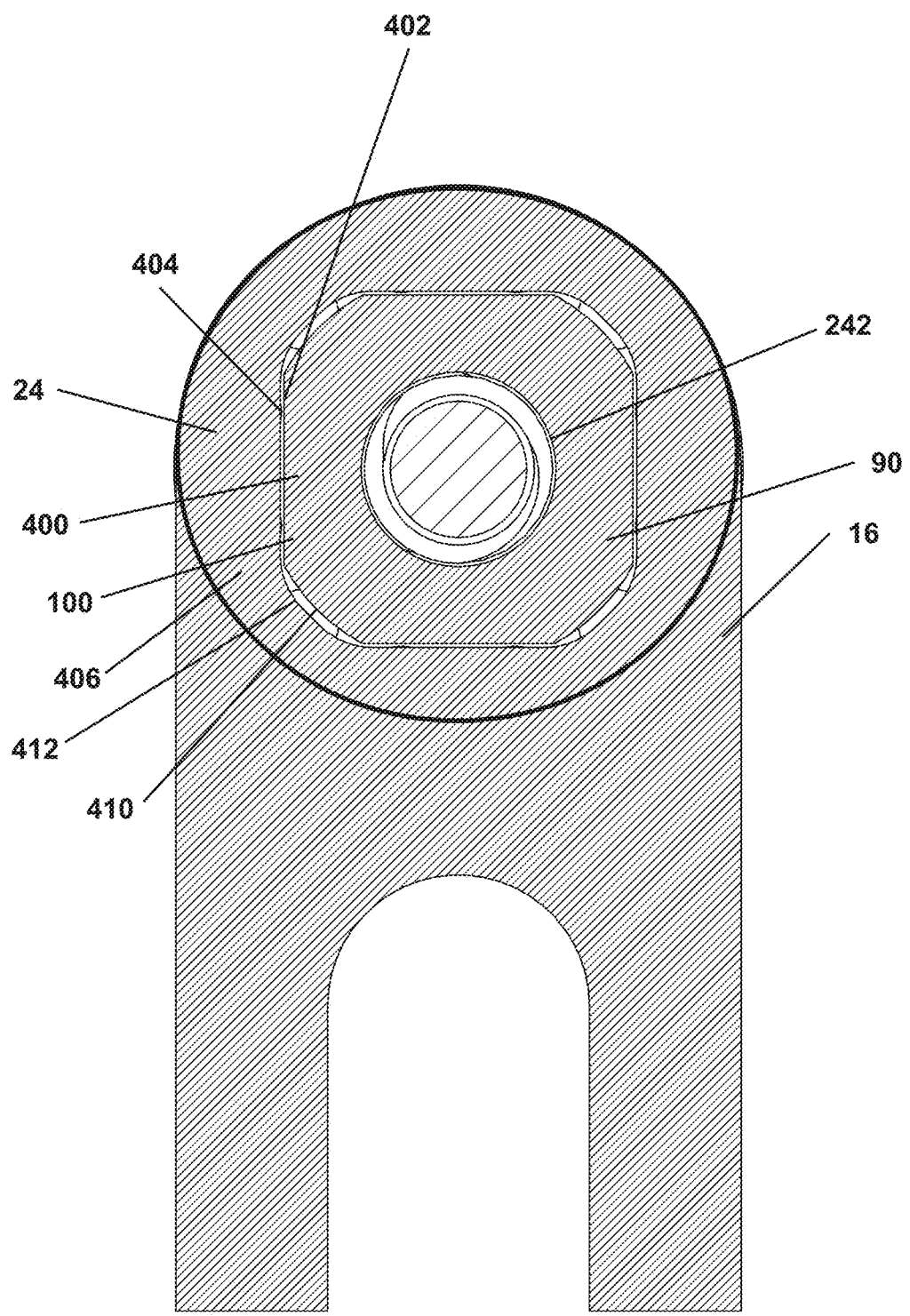
FIG. 9 is a cross-sectional view taken across line 9-9 in FIG. 4 showing a mating engagement between a mounting portion of the outer sleeve and a receiving portion of the handle that resists turning of the outer sleeve relative to the handle.

With reference to FIGS. 3 and 9, the mounting portion 100 of the sleeve 90 and the through opening 102 of the handle 16 are selected to provide a non-rotatable connection between the mounting portion 100 and the receiving portion 24. In one embodiment, the mounting portion 100 of the sleeve 90 has a non-circular cross-section taken perpendicular to the longitudinal axis 38, such as a substantially square cross-sectional shape. Likewise, the through opening 102 of the handle receiving portion 24 has a non-circular shape, such as a substantially square cross-sectional shape. In the embodiment of FIG. 9, the mounting portion 100 of the sleeve 90 includes one or more side portions 400 having one or more flat surfaces 402 in confronting relation with one or more flat surfaces 404 of one or more side walls 406 of the receiving portion 24. The mounting portion 100 of the sleeve 90 may include one or more junctures, such as tapered corners 410, connecting the flat surfaces 402. The receiving portion 24 may likewise have one or more corner portions 412 connecting the side walls 406 and extending about the mounting portion 100.

With reference to FIG. 11, there is a stop 420 between the inner shaft 104 and the sleeve 90 that limits proximal movement of the inner shaft 104 beyond the closed position. More specifically, the sleeve 90 includes an upper wall 422 and a lower wall 424. Each arm 44 includes a support portion 426. The stop 420 includes surfaces 428, 430 of the arm support portion 426 and surfaces 432, 434 of the walls 422, 424. The surfaces 428, 432 and 430, 434 abut to limit proximal movement of the inner shaft 104. Further, when the inner shaft 104 is in the closed position, the engaged surfaces 428, 432 and 430, 434 permits the sleeve 90 to transmit impact forces in direction 152 from the handle 16 directly into the support portion 426 of the arms 428. In this manner, the arms 44 may have thinner, resilient fork portions 435 of the arms 44 (see FIG. 3) that may not need to withstand impact forces.

The support portions 426 of the arms 44 together define a socket 440 that receives a boss 442 of the implant 20. The engagement between the boss 442 and the socket 440 increases the length of the engagement between the arms 44 and implant 20 along the longitudinal axis 38 of the implant 20. The increased longitudinal engagement strengthens the connection between the inserter tool 20 and the implant 10 against bending moments applied by the surgeon as the surgeon moves the inserter tool 10 in cephalad/caudal directions while maneuvering the implant 20 into an intervertebral space.

Figure 13:
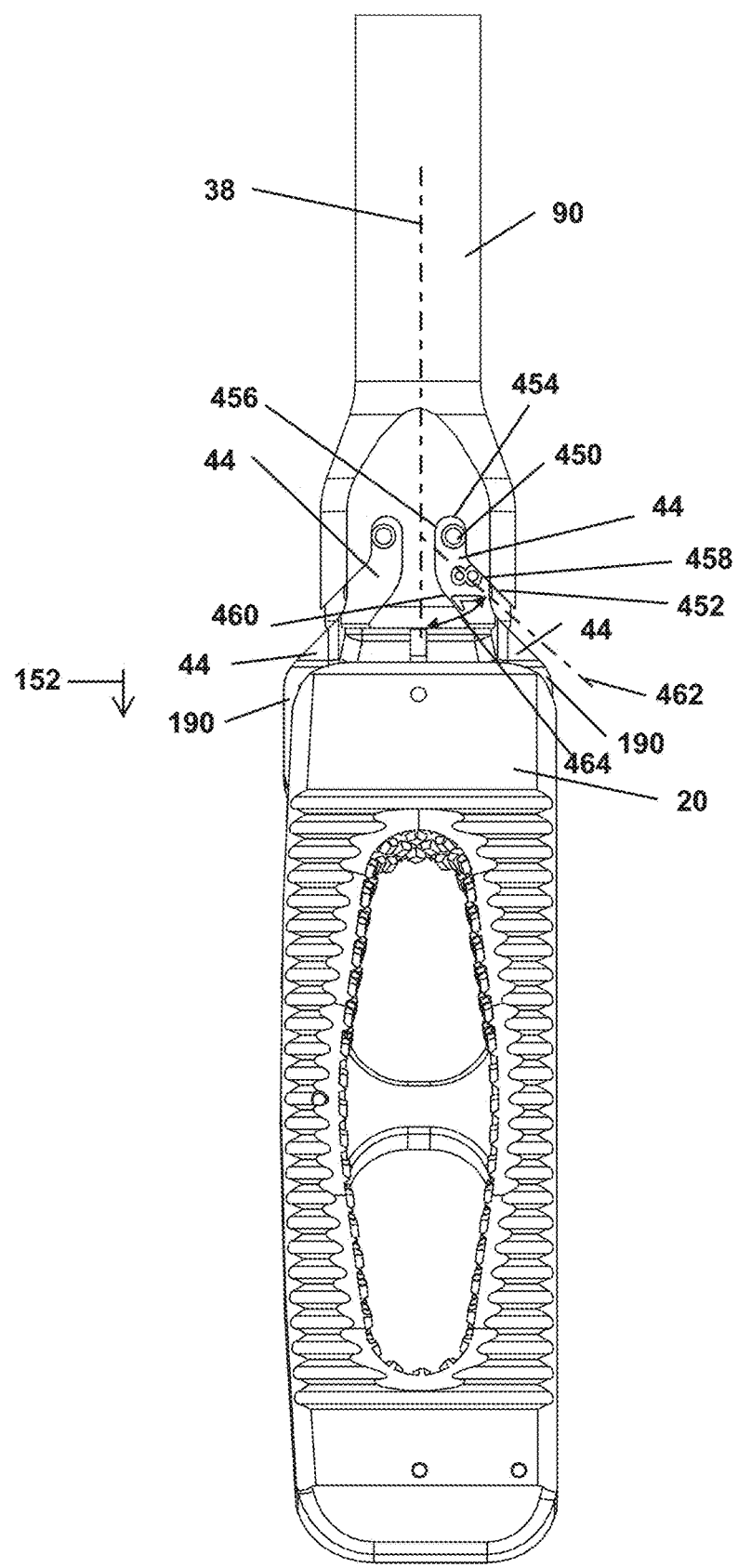
FIGS. 13, 14, and 15 show the inner shaft being shifted distally relative to the outer sleeve and pins of the arms cammingly engaging grooves of the outer sleeve to positively laterally urge the arms apart and disengage the inserter tool from the implant.
Figure 14:
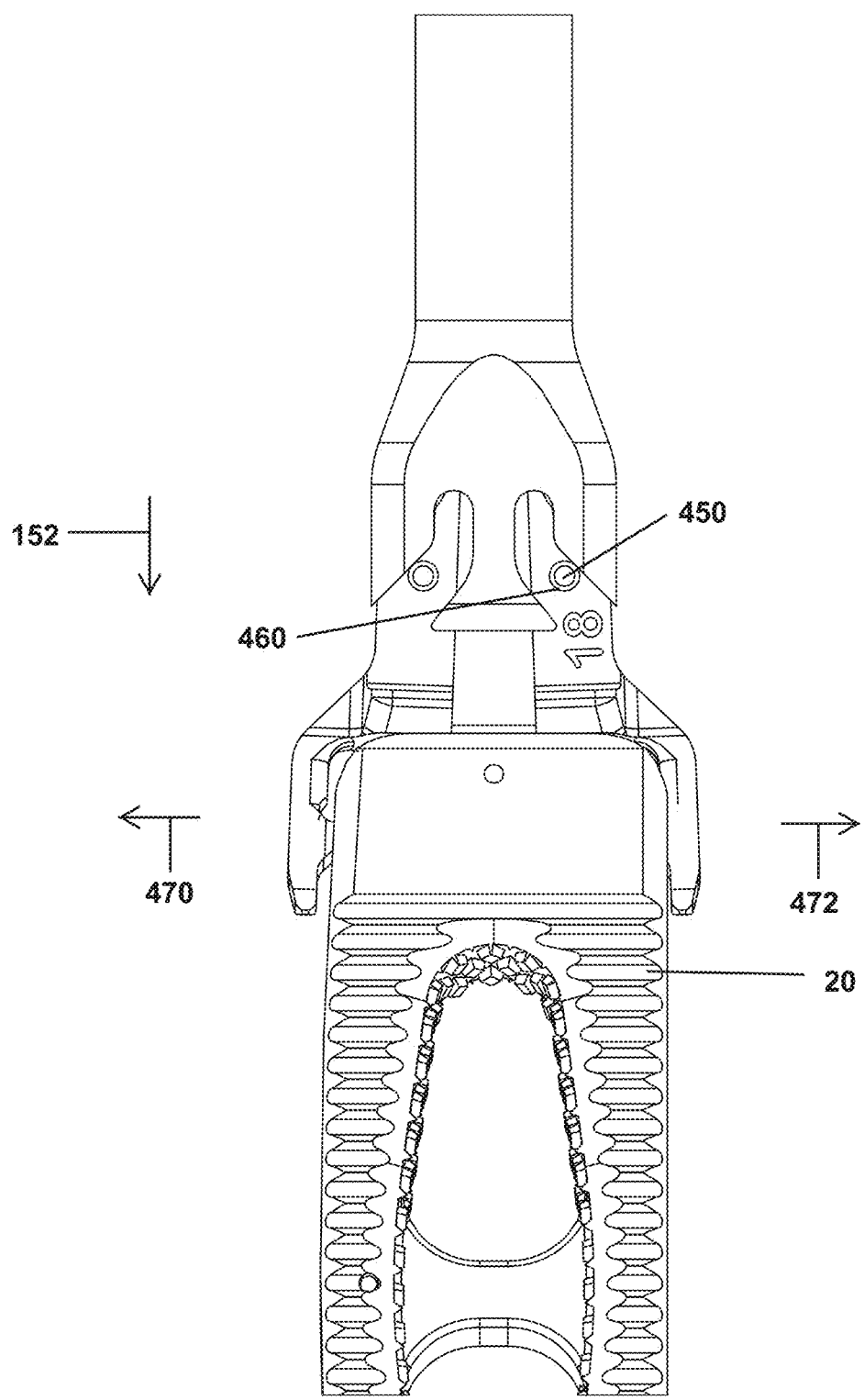
Figure 15:
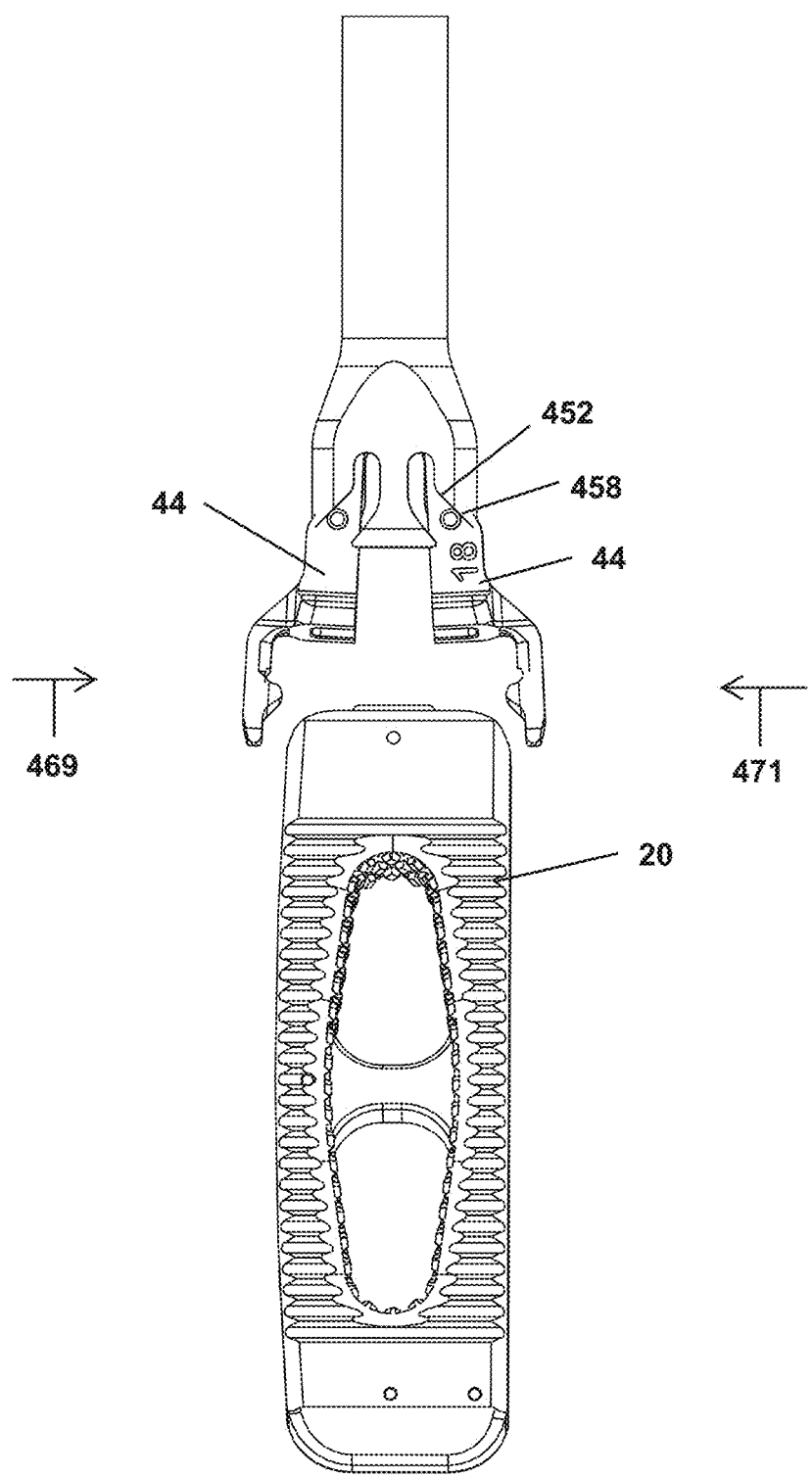

With reference to FIGS. 13-15, in some circumstances, the resilient properties of the fork portion 154 may be insufficient to separate the gripping portions 190 of the arms 44 from an implant 20 to release the implant 20. For example, a surgeon may form an opening in an annulus for receiving the implant 20 that is only as wide as the implant 20 and does not provide sufficient clearance for the gripping portions 190 to laterally disengage from the implant 20. To provide mechanical separation of the arms 44, the inserter tool 10 includes a cam follower, such as a pin 450 that rides along a cam, such as a cam surface 460 of a slot 452 of the sleeve 90. In one embodiment, each arm 44 has a pin 450 that rides in a respective slot 452. Each slot 452 includes an end 454, a longitudinal portion 456, and a transverse portion 458. The cam surface 460 of each slot 452 extends along an axis 462 at an angle 464 relative to the longitudinal axis 38. The angle 464 may be in the range of, for example, approximately 20 degrees to approximately 50 degrees, such as approximately 40 degrees.

Initially, in FIG. 13, the inner shaft 104 is shown in the closed position with the arms 44 held together by the sleeve 90. In FIG. 14, the user has turned the knob 231 to shift the inner shaft 104 distally in direction 152. Due to the presence of tissue resisting lateral expansion of the arms 44, the pins 450 are pressed against the cam surfaces 460 of the sleeve 90 which cams the arms 44 apart in lateral directions 470, 472. In FIG. 15, the user has shifted the inner shaft 104 to the open position and the arms 44 have disengaged from the implant 20.

Figure 16:
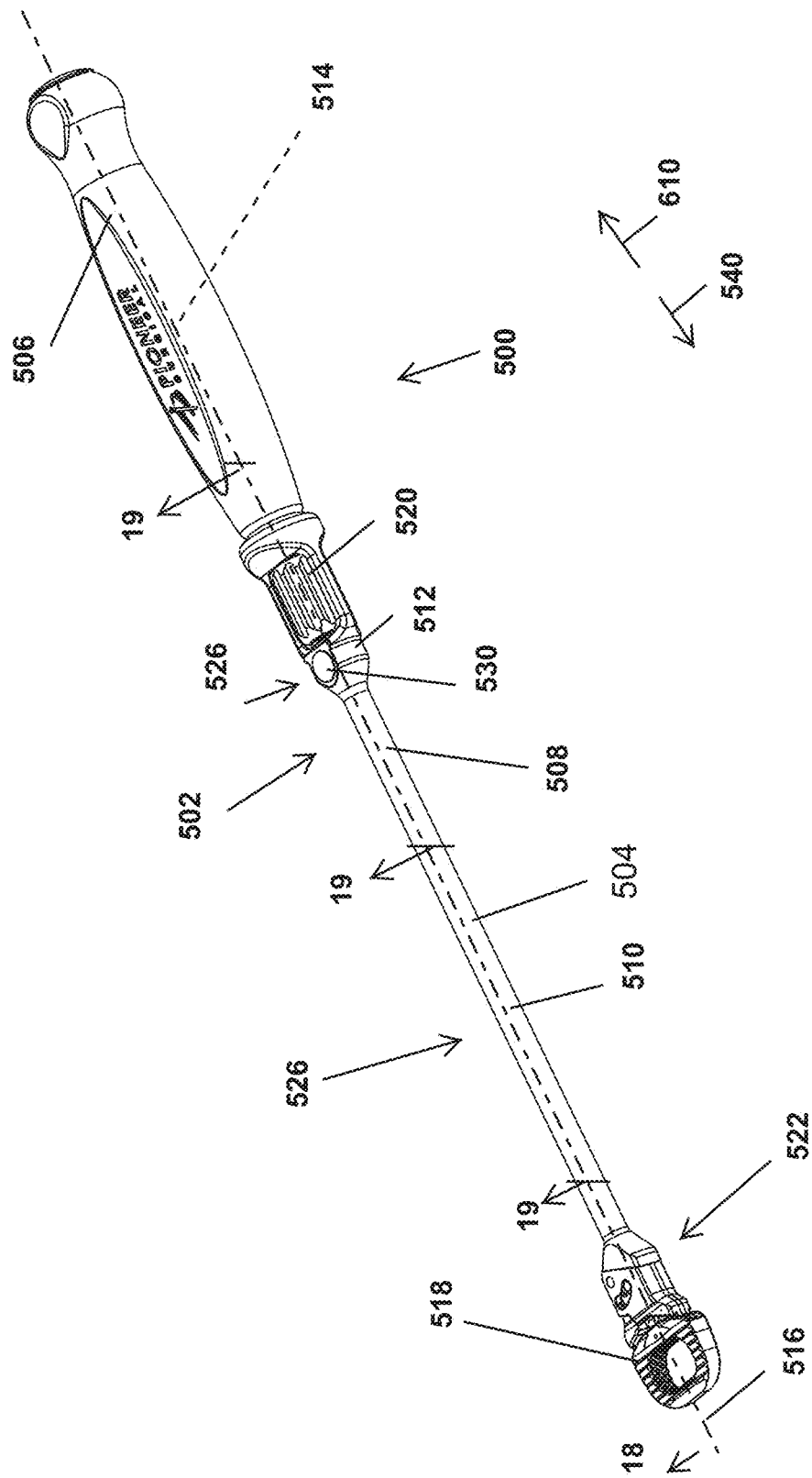
FIG. 16 is a perspective view of an inserter tool for inserting an implant.

With reference to FIG. 16, an inserter tool 500 is shown that is similar in many respects to the inserter tool 10 discussed above such that differences between the two will be highlighted. The inserter tool 500 includes a shaft 504 and a handle 506. The inserter tool 500 has a body 502 that includes a housing 508 with a sleeve 510 and a knob housing portion 512. The inserter tool 500 has a longitudinal tool axis 514 that is coaxially aligned with a longitudinal axis 516 of an implant 518 when the inserter tool 500 is connected to the implant 518. The inserter tool 500 includes an actuator, such as a knob 520, that is operated to shift a distal end portion 522 of the inserter tool 500 from an unlocked or open configuration that permits the implant 518 to be connected to the inserter tool 500 to a locked or closed configuration that secures the implant 518 to the inserter tool 500. The inserter tool 500 includes an inner shaft 524 (see FIG. 17) and a release mechanism 526 for selectively permitting removal of the inner shaft 524 from within the sleeve 510. Regarding FIG. 17, the release mechanism 526 includes a blocking body, such as a button 530, a spring 532, and a retainer 534. The retainer 534 keeps the button 530 within a release compartment 536 of the housing 508. The release mechanism 526 operates in a manner substantially similar to the release mechanism 170 discussed above. For example, the button 530 may contact a collar 538 of the inner shaft 524 to limit movement of the inner shaft 524 in a distal direction 540.

Figure 17:
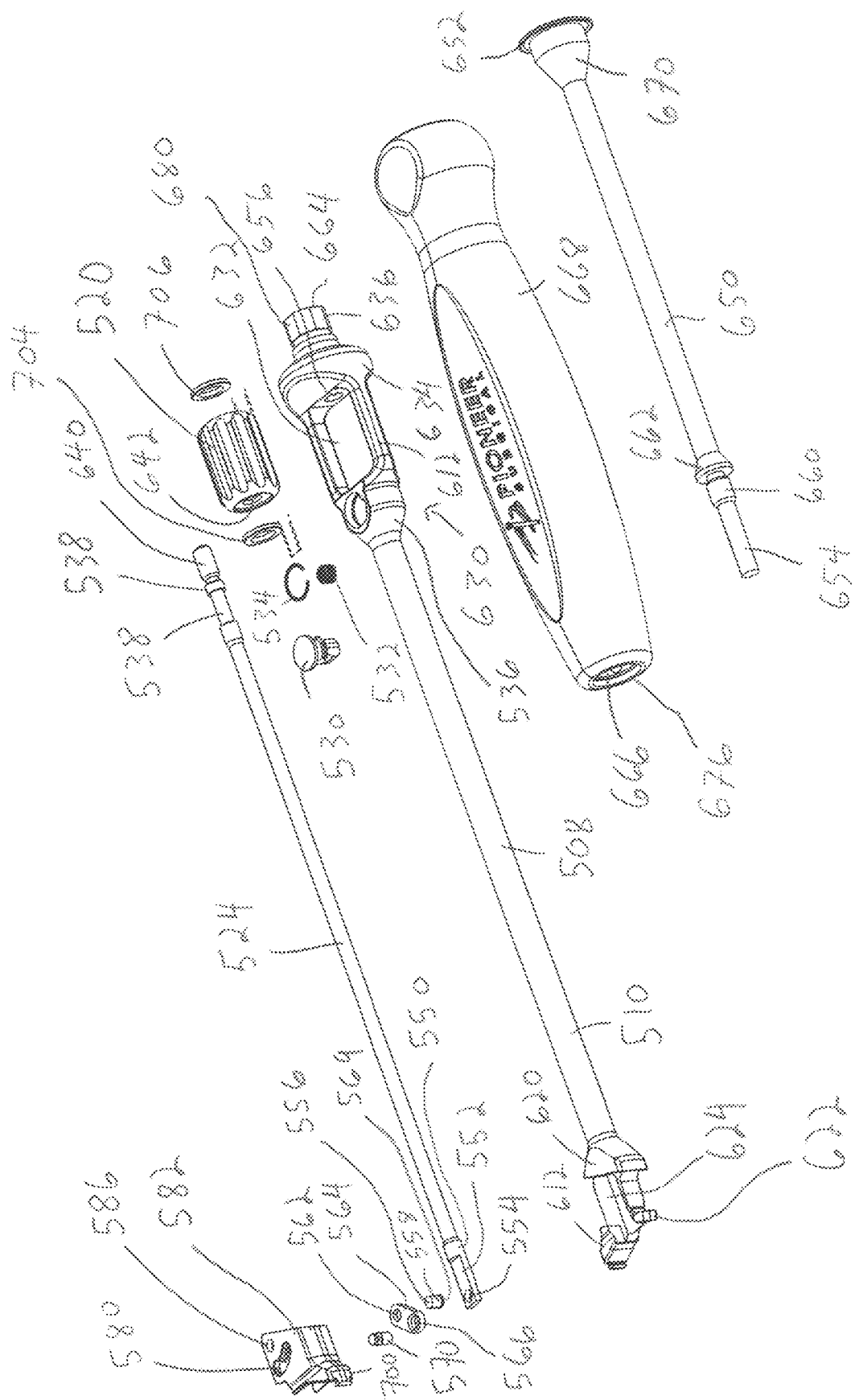
FIG. 17 is an exploded view of the inserter tool of FIG. 16 showing an inner shaft, an outer sleeve, a handle, and an impact shaft of the inserter tool.
Figure 18:
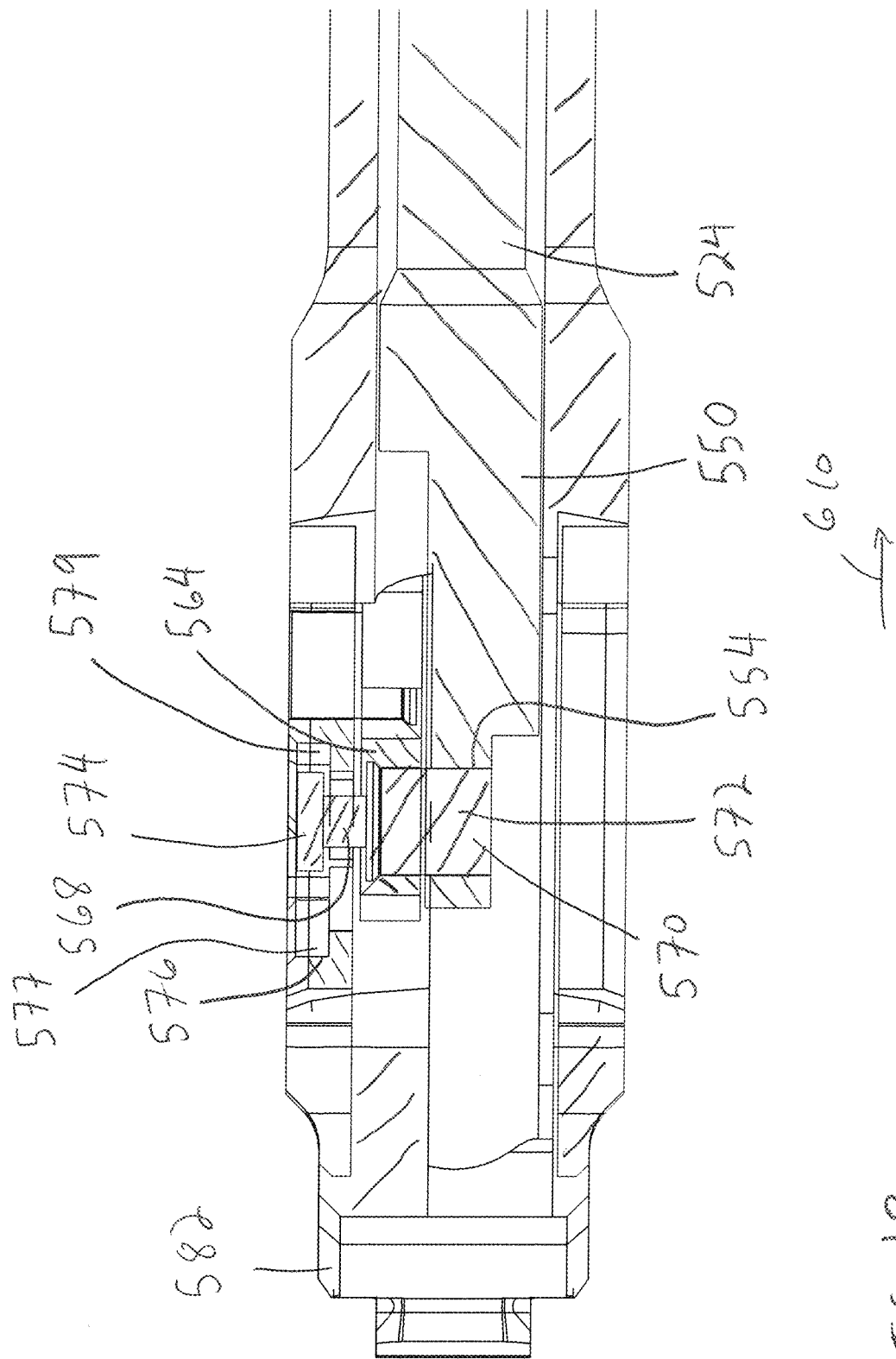
FIG. 18 is a cross-sectional view taken across line 18-18 in FIG. 16 showing the inner shaft extending in the housing and connected via a pin and a link to a movable gripping body.

With reference to FIGS. 17 and 18, the inner shaft 524 includes a connecting portion 550 having a flat 552 and a hole 554 that receives a body 572 of a pin 570. The body 570 of the pin 570 also extends through a hole 566 of a link 564. The pin 570 pivotally connects the link 564 to the inner shaft connecting portion 550. The pin 570 further has a neck 568 that extends in an arcuate elongated path, such as slot 580, of a movable gripping body 582 and a head 574 received in an upper portion 576 of the slot 580. In one embodiment, the neck 568 and head 574 generally do not contact sides 577, 579 of the slot 580 as the distal end portion 522 is shifted between open and closed configurations. In other embodiments, the neck 568 and/or the head 574 may contact one or more sides 577, 579 of the slot 580.

At an opposite end of the link 564 from the pin 570, the distal end portion 522 includes a pin 558. The pin 558 has a lower portion 569 received in a hole 562 of the link 564 and an upper portion 556 received in a hole 586 of the gripping body 582. The pin 558 is configured to pivotally connect the link 564 to the gripping body 582.

Figure 24:
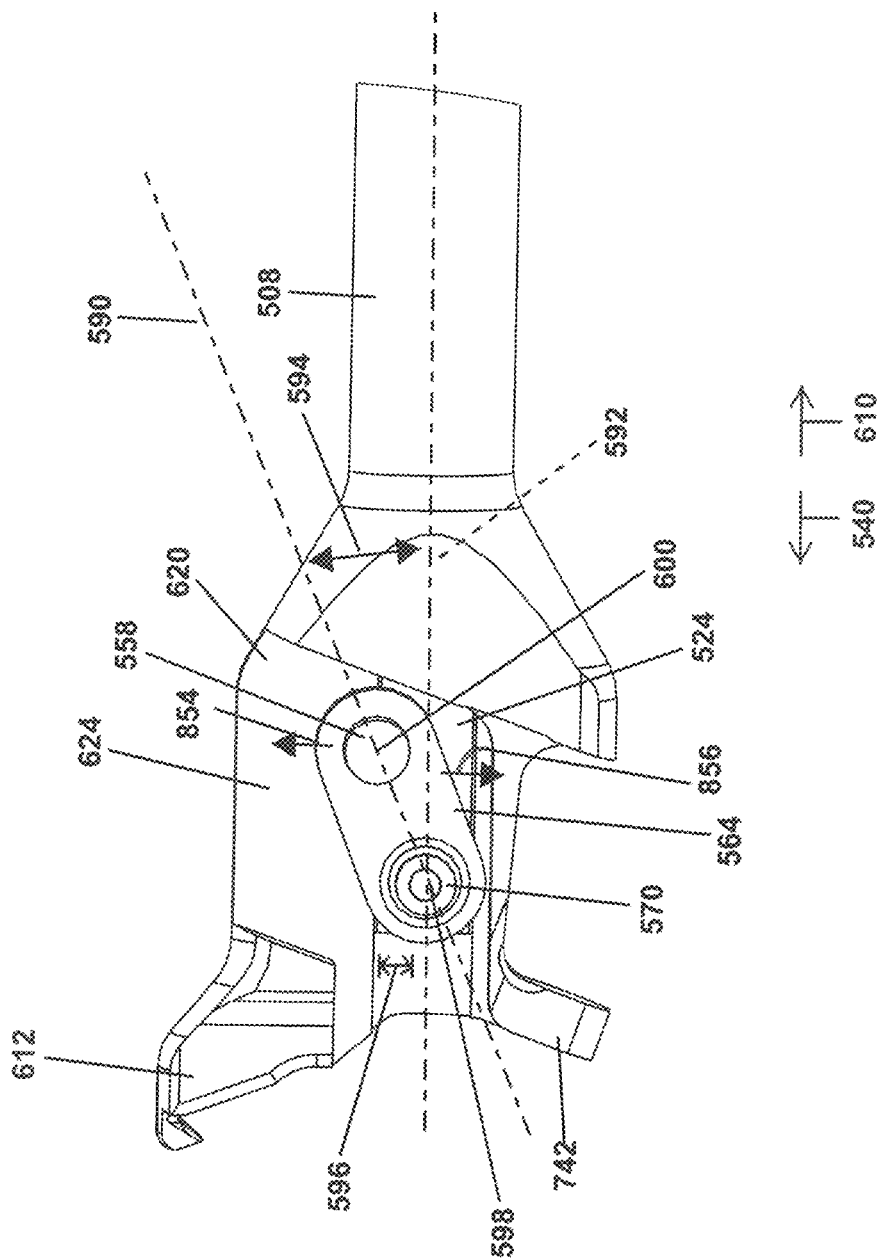
FIG. 24 is a top plan view similar to FIG. 22 except with the movable gripping body removed to show the inner shaft, the link, and the pins.

With reference to FIG. 24, the link 564 has a longitudinal axis 590 and the inner shaft 524 has a longitudinal axis 592. The axes 590, 592 are at an angle 594 relative to one another so that there is an offset distance 596 between a center 598 of the pin 570 and a center 600 of the pin 558. When the inner shaft 524 is shifted proximally in direction 610, the link 564 pivots counterclockwise as shown in FIG. 24 due to the pivotal connection between the pin 558 and the gripping body 582. Counterclockwise pivoting of the link 564 increases the angle 594 and shifts the gripping body 582 toward an arm 612 of the sleeve 510. Conversely, shifting the inner shaft 524 in distal direction 614 decreases the angle 594 between the axes 590, 592 which shifts the gripping body 582 away from the arm 612.

Returning to FIG. 17, the sleeve 510 includes a guide portion 620 that includes the arm 612, a guide member 622, and a land 624 that supports and guides the gripping body 582 as the gripping body 582 shifts between open and closed positions.

At a proximal end portion 630 of the housing 508, there is an opening 632 that receives the knob 520 and a flared portion 634 from which a receiving portion 636 projects proximally. The inner shaft 524 includes a threaded portion 640 that engages threads of an inner bore 642 of the knob 520. Thus, turning the knob 520 in first direction causes the inner shaft 524 to shift proximally in direction 610 whereas turning the knob 520 in a second direction causes the inner shaft 524 to shift distally in the direction 540. The inserter tool 500 may include washers 704, 706 that separate the knob 520 and the housing 508 that reduces wear between the knob 520 and housing 508 and makes turning of the knob 520 easier.

The inserter tool 500 also includes an impact shaft 650 having an impact surface 652 for receiving impacts, such as from a hammer, to advance the implant 518 into an intervertebral space. The impact shaft 650 includes a support portion 654 that extends through a through opening 656 of the housing 508 and into a proximal end of the bore 642 of the knob 520. During assembly of the inserter tool 500, the support portion 654 is advanced distally through a through bore 666 of the handle 668 and into the through opening 656 of the housing 508. The support portion 654 rotatably supports the proximal end of the knob 520 while the threaded portion 640 of the inner shaft 524 rotatably supports an opposite end of the knob 520. The impact shaft 650 has a threaded portion 660 that is engaged with internal threads of the receiving portion 636 of the housing 508 to secure the impact shaft 650 to the housing 508. Additionally or alternatively, the impact shaft 650 may be welded, epoxied, and/or secured using one or more fasteners to the housing 508. The impact shaft 650 further includes a shoulder 662 that seats against an end surface 664 of the receiving portion 636. The impact shaft 650 includes a frustoconical portion 670 that mates with a similarly configured receptacle of a proximal end of the handle 668.

Regarding FIG. 17, the handle 668 includes a socket 676 that fits over the receiving portion 636 of the housing 508. The socket 676 may be configured to mate with the receiving portion 636 to form a non-rotatable connection therebetween. In one approach, the receiving portion 636 includes one or more flats 680 that abut against corresponding flats of the socket 676 to resist rotation of the handle 668 relative to the housing 508.

Figure 19:
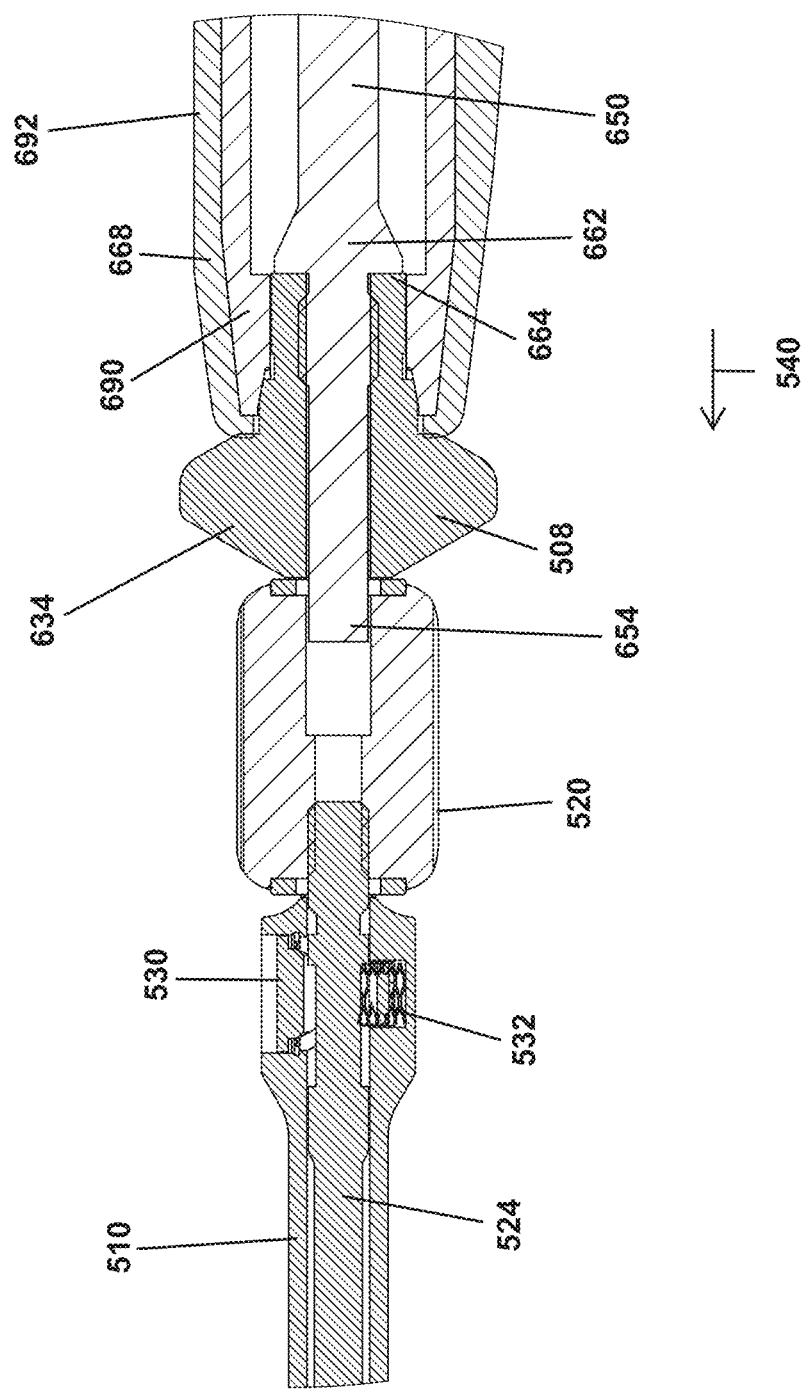
FIG. 19 is a cross-sectional view taken across line 19-19 in FIG. 16 showing a release mechanism of the instrument that retains the inner shaft within the housing.

Regarding FIGS. 17 and 19, the handle 668 may have a core 690 made of a rigid material that may be light and strong, such as aluminum, and an outer layer 692, such as silicone, that is easily gripped by a surgeon. When an impact is applied in direction 540 against the impact surface 652 of the impact shaft 650, the shoulder 662 abuts the end surface 664 of the housing 508 and transmits the impact to the housing 508. The housing 508 in turn transmits the impact force to the sleeve 510 and the gripping body 582. The sleeve 510 and gripping body 582 apply the impact force against the implant 518.

Figure 20:
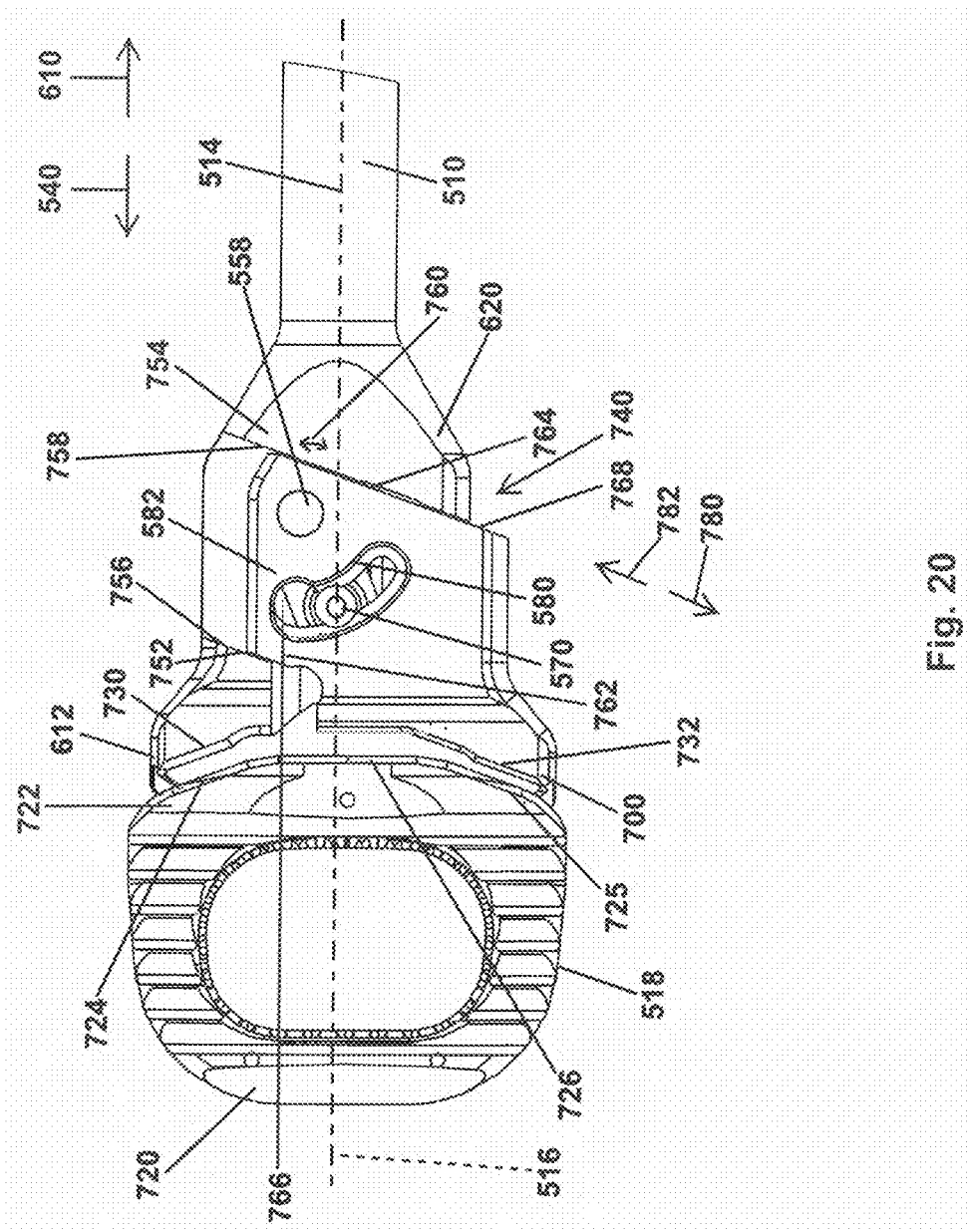
FIG. 20 is a top plan view of the distal end of the inserter tool of FIG. 16 showing the implant gripped between an arm of the housing and an arm of the movable gripping body.

With reference to FIG. 20, the implant 518 includes a leading end portion 720 and a trailing end portion 722 with the longitudinal axis 516 extending therebetween. The trailing end portion 722 includes a pair of transversely extending rear walls 724, 725 and a rear wall 726. The sleeve 510 includes the arm 612 and the gripping body 582 includes an arm 700. The arms 621, 700 include walls 730, 732 that are complementary to the walls 724, 725. The walls 730, 732 support and resist turning of the implant 518 relative to the inserter tool 500.

Figure 23:
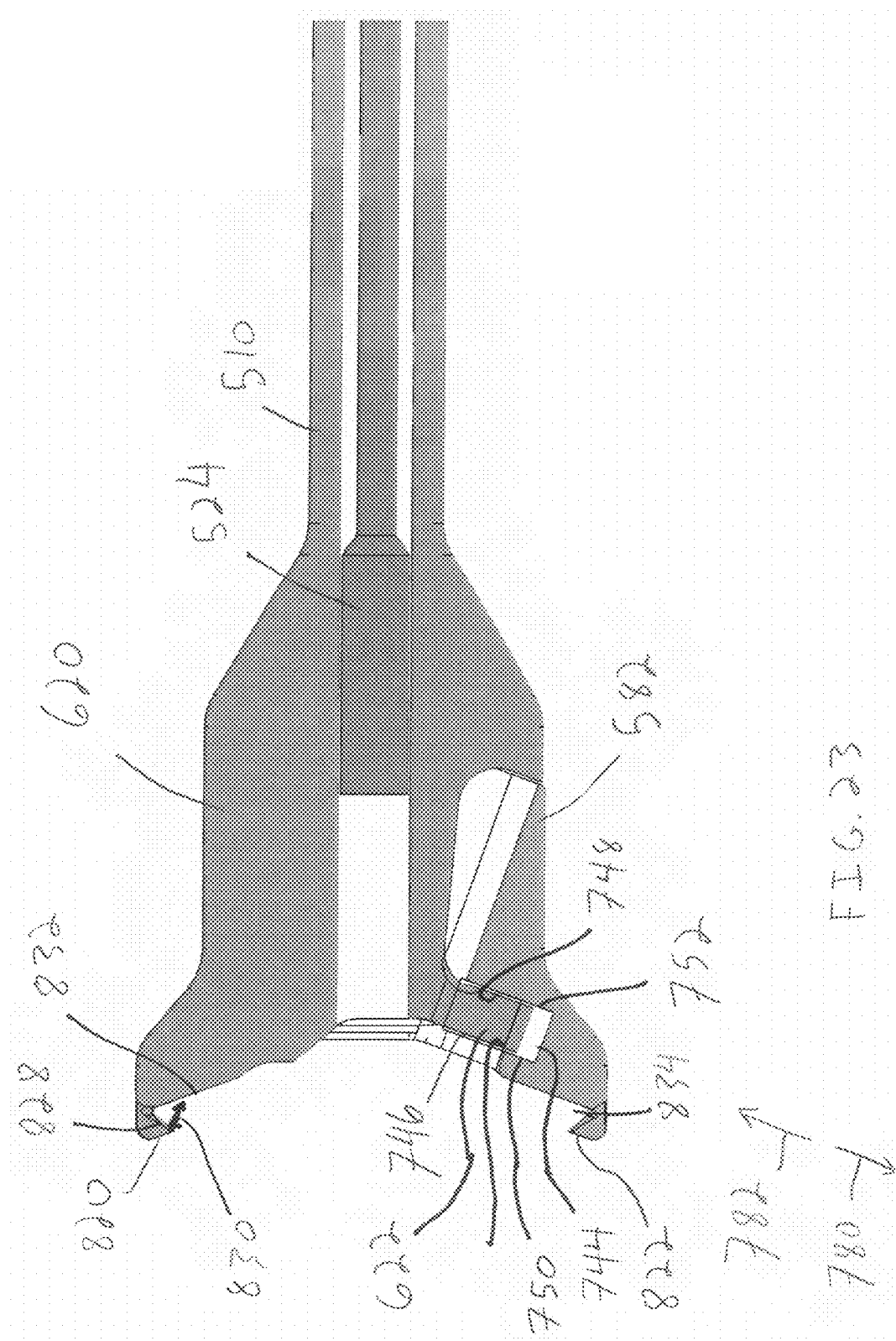
FIG. 23 is a cross-sectional view taken across line 23-23 in FIG. 21 showing a slide connection between the housing and the movable gripping body that includes a guide member of the housing extending into a slot of the movable gripping body to guide the gripping body as the gripping body moves between opened and closed positions.

With reference to FIGS. 20 and 23, the distal end portion 522 of the inserter tool 500 includes a slide connection 740 between the gripping body 582 and the sleeve 510 that guides the gripping body 582 along a predetermined path relative to the guide portion 620 of the sleeve 510. In one embodiment, the slide connection 740 includes the guide member 622 (see FIG. 23) of the sleeve guide portion 620 that extends transversely relative to the longitudinal axis 514 and into a slot 744 of the gripping body 582. The guide member 622 includes opposite surfaces 746, 748 that permit surfaces 750, 752 of the gripping body 582 to slide therealong. In one embodiment, the surfaces 746, 750 and 748, 752 are flat, confronting surfaces.

The slide connection 740 may also include walls 752, 754 (see FIG. 20) of sleeve guide portion 620 having inclined surfaces 756, 758 that each extend at an angle 760 relative to the longitudinal axis 514. The angle 760 may be in the range of, for example, approximately 30 to approximately 90 degrees, such as approximately 70 degrees. The gripping body 582 likewise has walls 762, 764 with surfaces 766, 768 that slide along the inclined surfaces 756, 758 of the sleeve guide portion 620. In one embodiment, the surfaces 756, 766 and 758, 768 include abutting flat portions.

The sliding contact between the gripping body 582, the guide member 622, and the walls 752, 754 restrict movement of the gripping body 582 to a linear movement in a direction 780 toward an open position or direction 782 toward a closed position.

Figure 21:
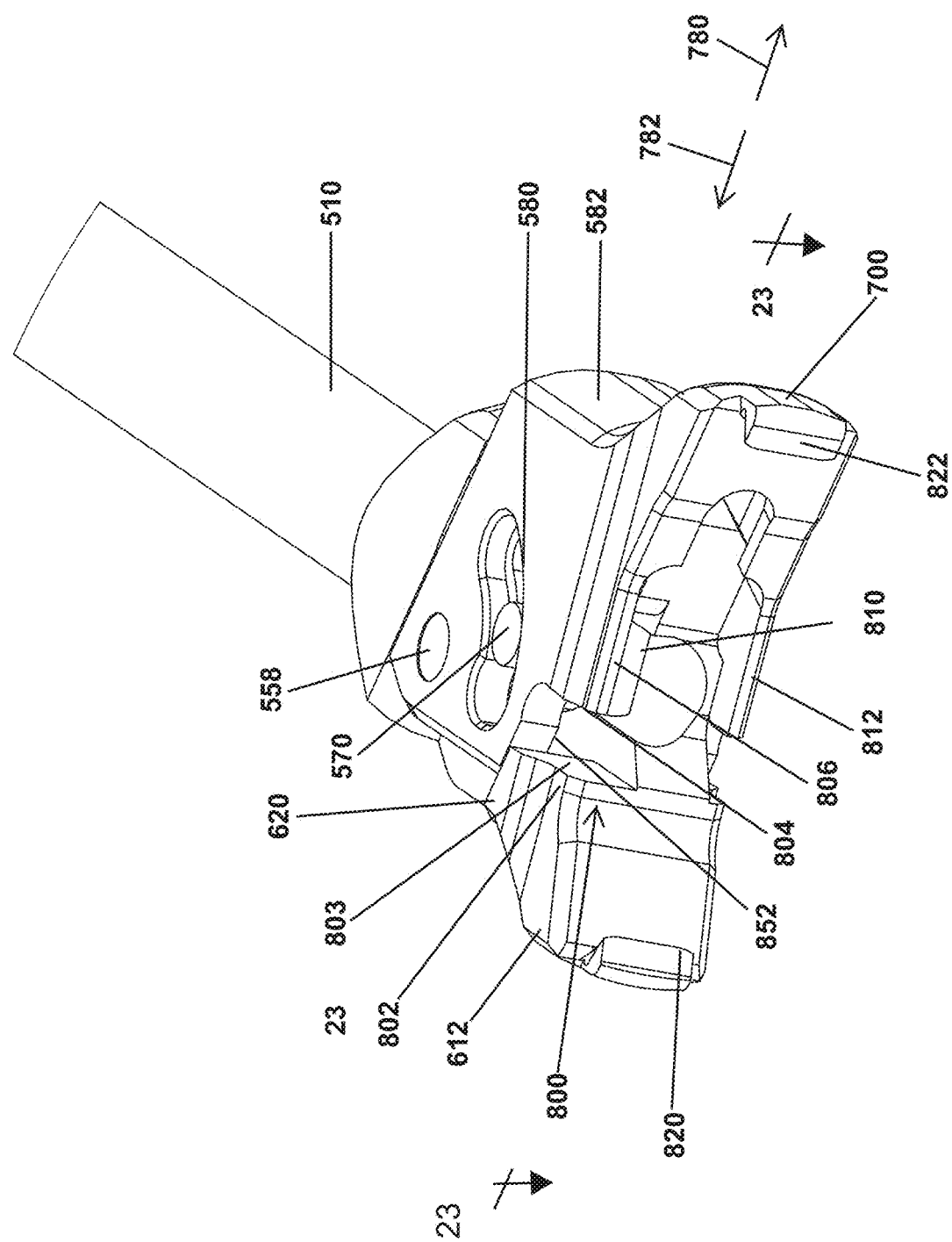
FIG. 21 is a perspective view of the distal end of the inserter tool of FIG. 16 showing fingers of the housing and the gripping body that fit into undercuts of the implant to connect the inserter tool to the implant.
Figure 22:
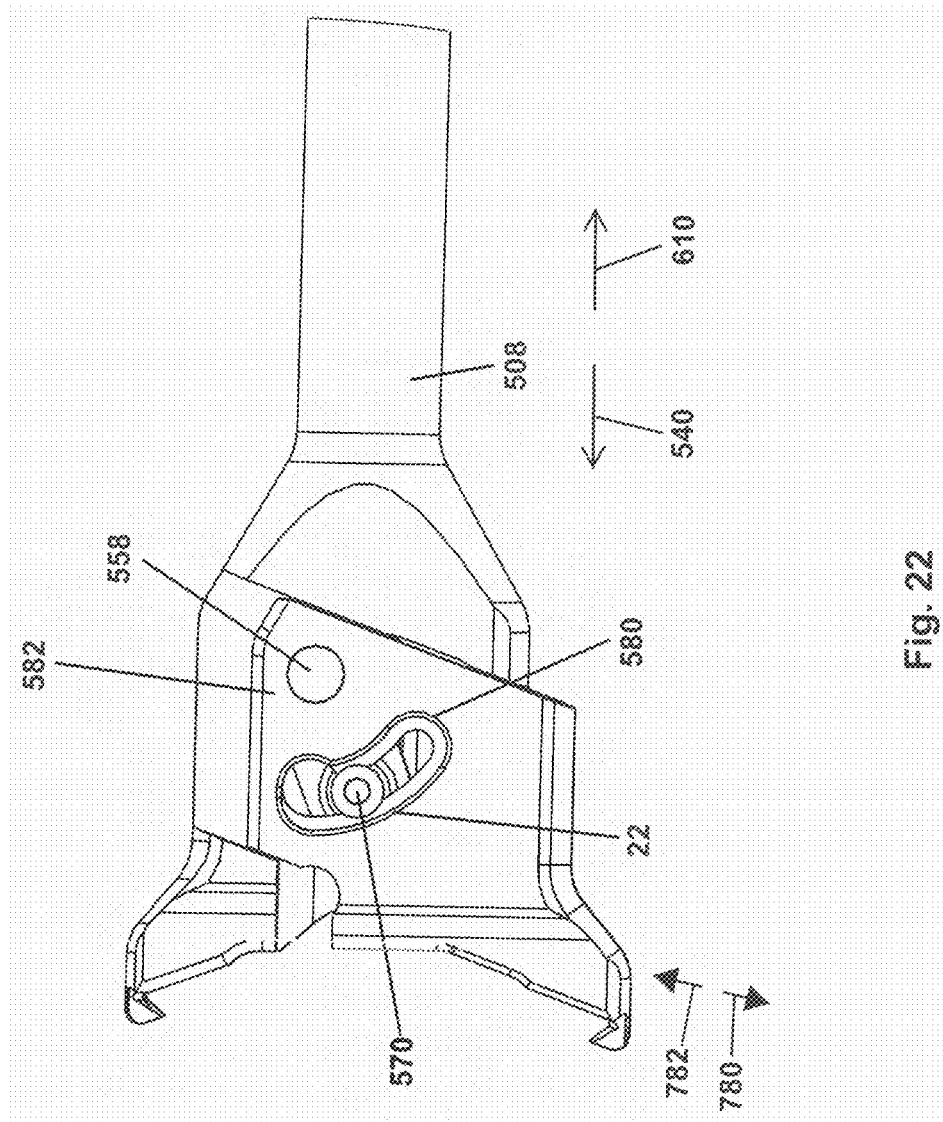
FIG. 22 is a top plan view of the distal end of the inserter tool of FIG. 16 showing the pin that connects the inner shaft to the link received in an elongated slot of the movable gripping body and another pin connected to the link received in a hole of the movable gripping body.

With reference to FIG. 21, the distal end portion 522 of the inserter tool 500 includes a stop 800 that limits movement of the gripping body 582 in direction 782 to a fully closed position. In the fully closed position, the gripping body 582 is farther in direction 782 beyond the closed position of the gripping body 582. The presence of the implant 518 limits movement of the gripping body 582 to the closed position but, when the implant 518 is removed from the inserter tool 500, the gripping body 582 may be shifted to the fully closed position. Because the fully closed position is beyond the closed direction in direction 782, the distance between the closed and fully closed positions permits the gripping body 582 to securely clamp the implant 518 between the arms 612, 700 while taking up any variation in tolerances of the geometry of the implant 518.

In one embodiment, the stop 800 includes a wall 802 of the guide portion 620 having a surface 803 that abuts and limits movement of a surface 804 of a wall 806 of the gripping body 582 in the closing direction 782. Conversely, the inserter tool 500 has a hard stop to limit shifting of the gripping body 582 in the opening direction 780 by way of the collar 538 (see FIG. 17) contacting the button 530 when the button is in a blocking position. In the blocking position, the button 530 has a portion that is an axially overlapping relation with the collar 538 and inhibits shifting of the inner shaft 524 in distal direction 540 beyond a predetermined position.

Regarding FIGS. 20 and 21, the gripping body 582 includes a pair of central walls 810, 812 facing and spaced from the rear wall 726 of the implant 518. Further, the walls 730, 732 of the arms 612, 700 contact the walls 724, 725 of the implant 518. The abutting walls 730, 732 and the walls 724, 725, of the inserter tool 500 of the implant 518 transfer impacts from the impact surface 652 of the inserter tool 500 to the implant 518. Further, the contact between the walls 730, 732 of the inserter tool 500 and the walls 724, 725 of the implant 518 evenly distributes the impact forces around the trailing end portion 722 of the implant 518. This provides a durable connection between the implant 518 and the inserter tool 500.

With reference to FIGS. 21 and 23, the arms 612, 700 include fingers 820, 822 that fit into undercuts 824, 826 (see FIG. 30) of the implant 518. Regarding FIG. 23, each finger 820, 822 includes a surface 828 extending at an acute angle 830 relative to a surface 832 of the adjacent wall 730, 732. This forms an undercut 834 that receives a lip 750 (see FIG. 30) of the implant 518 when the fingers 820, 822 are received in the undercuts 824, 826. The overlapping engagement between the fingers 820, 822 and the lips 750, 752 resist axial separation of the implant 518 from the inserter tool 500.

With respect to FIG. 24, the guide portion 620 of the sleeve 510 includes the land 624 that supports an inner surface 852 (see FIG. 21) of the gripping body 582. The movement of the pin 558 applies a force generally in direction 854, 856 to the gripping body 582 depending on whether the inner shaft 524 is shifted in direction 540 or 610.

Figure 25B:
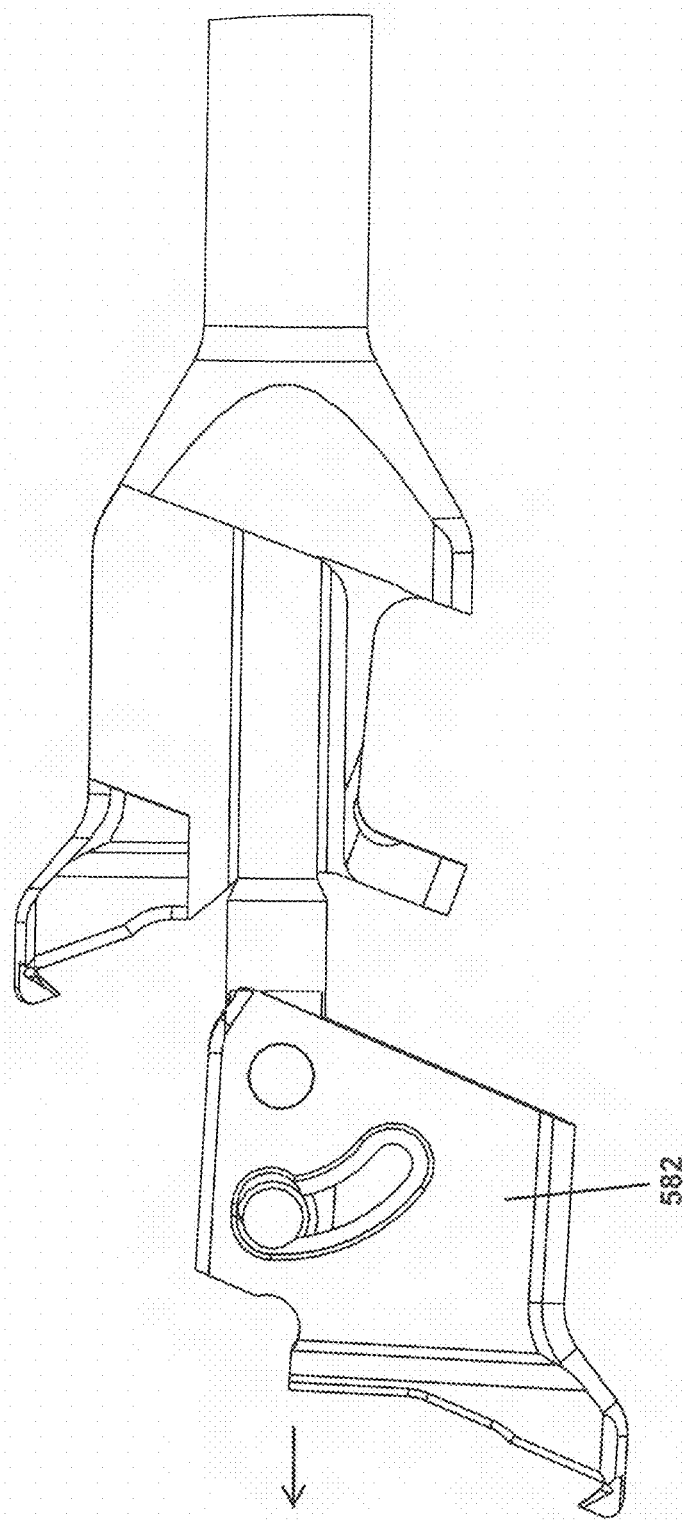

With reference to FIGS. 25A-28, the distal end portion 522 of the inserter tool 500 is shown in FIG. 25A in a removal configuration. The user has pressed the button 530 to position the button 530 in clearance with the collar 538 of the inner shaft 524 and has turned the knob 521 to urge the inner shaft 524 in distal direction 540 until the pin 570 is at an end portion 870 of the slot 580. With the pin 570 at the end portion 870, the link 564 is substantially longitudinally aligned with the connecting portion 550 of the inner shaft 524 and received on the flat 552 of the inner shaft 524. In this position, the gripping body 582 is shifted in direction 780 to a position wherein the guide member 742 no longer extends in the slot 744. With the guide member 742 removed from the slot 744, the gripping body 582 and the inner shaft 524 may be slid off in direction 540 as shown in FIG. 25B.

Regarding FIG. 26, the distal end portion 522 is shown in the open configuration wherein the pin 570 is at a first portion 872 of the slot 580 and the angle 594 between the longitudinal axes 590, 592 (see FIG. 24) of the link 564 and the inner shaft 524 is at a first angle. The implant 518 may be positioned so that the trailing end portion 722 thereof is positioned between the arms 612, 700.

With reference to FIG. 27, the user next turns the knob 521 in the locking direction to shift the inner shaft 524 proximally in direction 610. This causes the pin 570 to travel to a second position 874 along the slot 580 as the angle 594 between the axes 590, 592 of the link 564 and the inner shaft 524 increases from the first angle of FIG. 26. As discussed above, the pin 558 drives the gripping body 582 in direction 782 and reduces the distance between the arms 612, 700. In FIG. 27, the arms 612, 700 are shown in the closed configuration wherein the fingers 820, 822 are positioned to be engaged with the lips 750 of the implant 518 and the arms 612, 700 clamp the implant 518 therebetween.

Regarding FIG. 28, the implant 518 is not present between the arms 612,700 and the user has turned the knob 521 in the locking direction to shift the distal end portion 522 to a fully closed configuration. In the fully closed configuration, the surfaces 803, 804 of the arm 612 and the gripping body 582 are engaged to limit further travel of the gripping body 582 in direction 782. In the fully closed position, the fingers 820, 822 of the arms 612, 700 are positioned closer together than the lips 750 of the implant 518 would permit. Because the position of the gripping body 582 when the distal end portion 522 is in the fully closed configuration is beyond the position of the gripping body 582 when the distal end portion 522 is in the closed configuration, the gripping body 582 may take-up any dimensional variation in the trailing end portion 722 of the implant 518.

Figure 29:
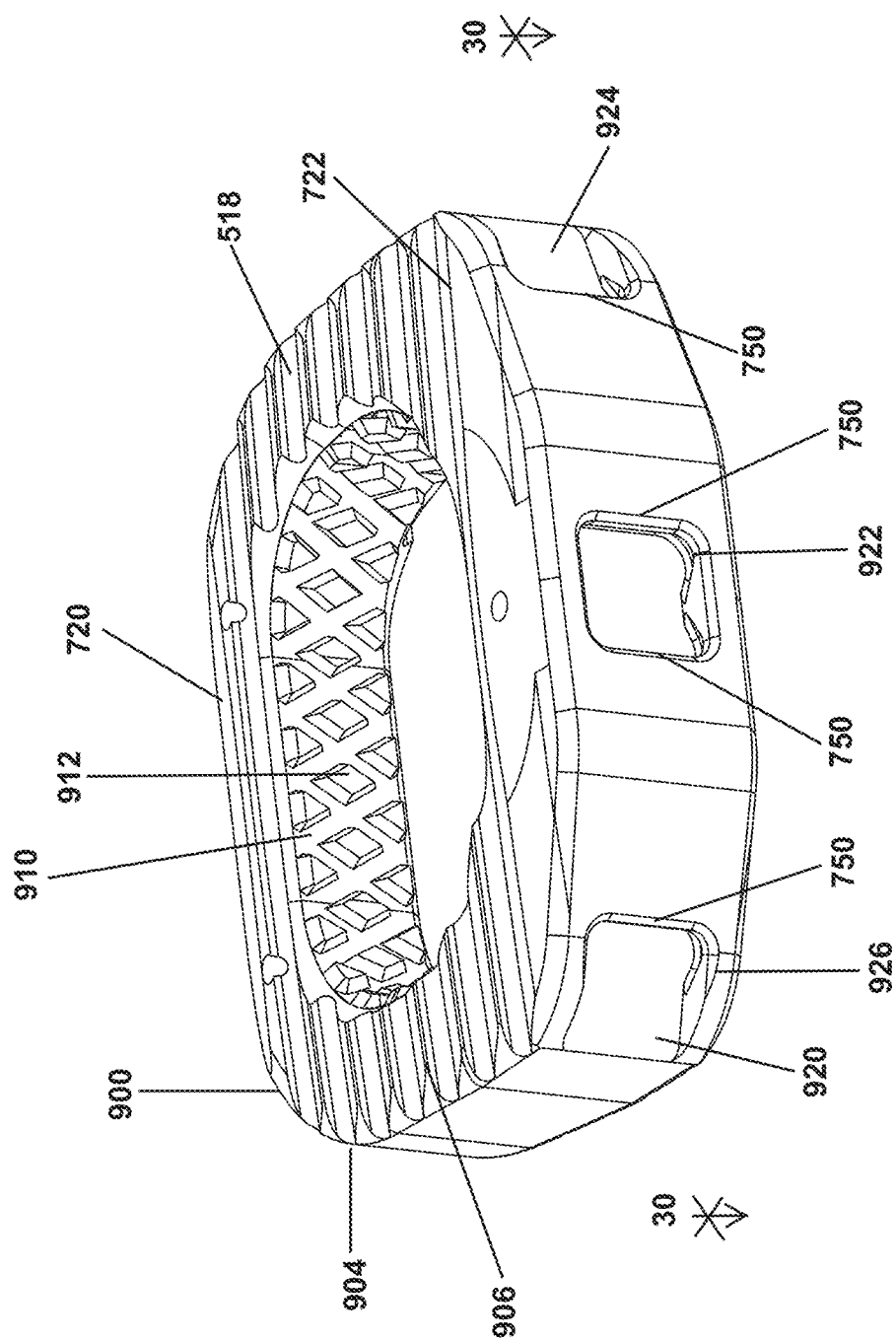
FIG. 29 is a rear perspective view of the implant of FIG. 16 showing a trailing end portion of the implant having pockets that permit different inserter tools to connect to the implant.
Figure 30:
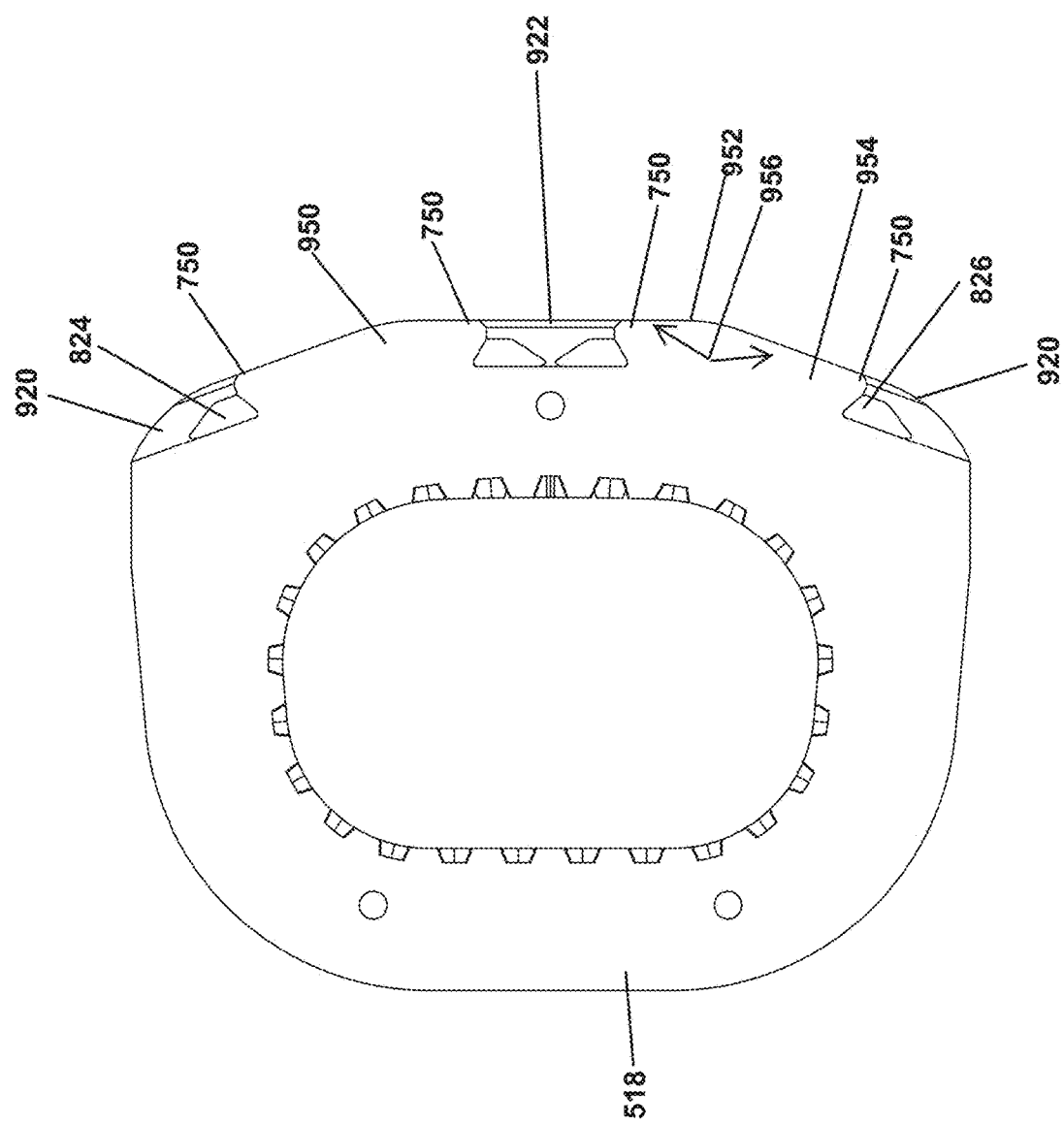
FIG. 30 is a cross-sectional view taken across line 30-30 in FIG. 29 showing pockets of the trailing end portion of the implant that include undercuts for receiving the fingers of the inserter tool of FIG. 16.

With reference to FIGS. 29 and 30, the implant 518 may be manufactured using an additive manufacturing approach. In one embodiment, the implant 518 is made of a PEKK or PEEK material that is laser sintered into the shape of the implant 518. The implant 518 includes a body 900 having an annular wall 904 extending about a central cavity 906. The wall 904 includes an inner surface 910 having a plurality of protrusions 912 that provide additional surface area for bone graft material to engage with. In other embodiments, the implant 518 may be made using a subtractive manufacturing approach, such as by machining the implant from a block of PEEK, and/or may be molded. In some embodiments, the implant 518 may be made of a metallic material such as titanium.

Figure 31:
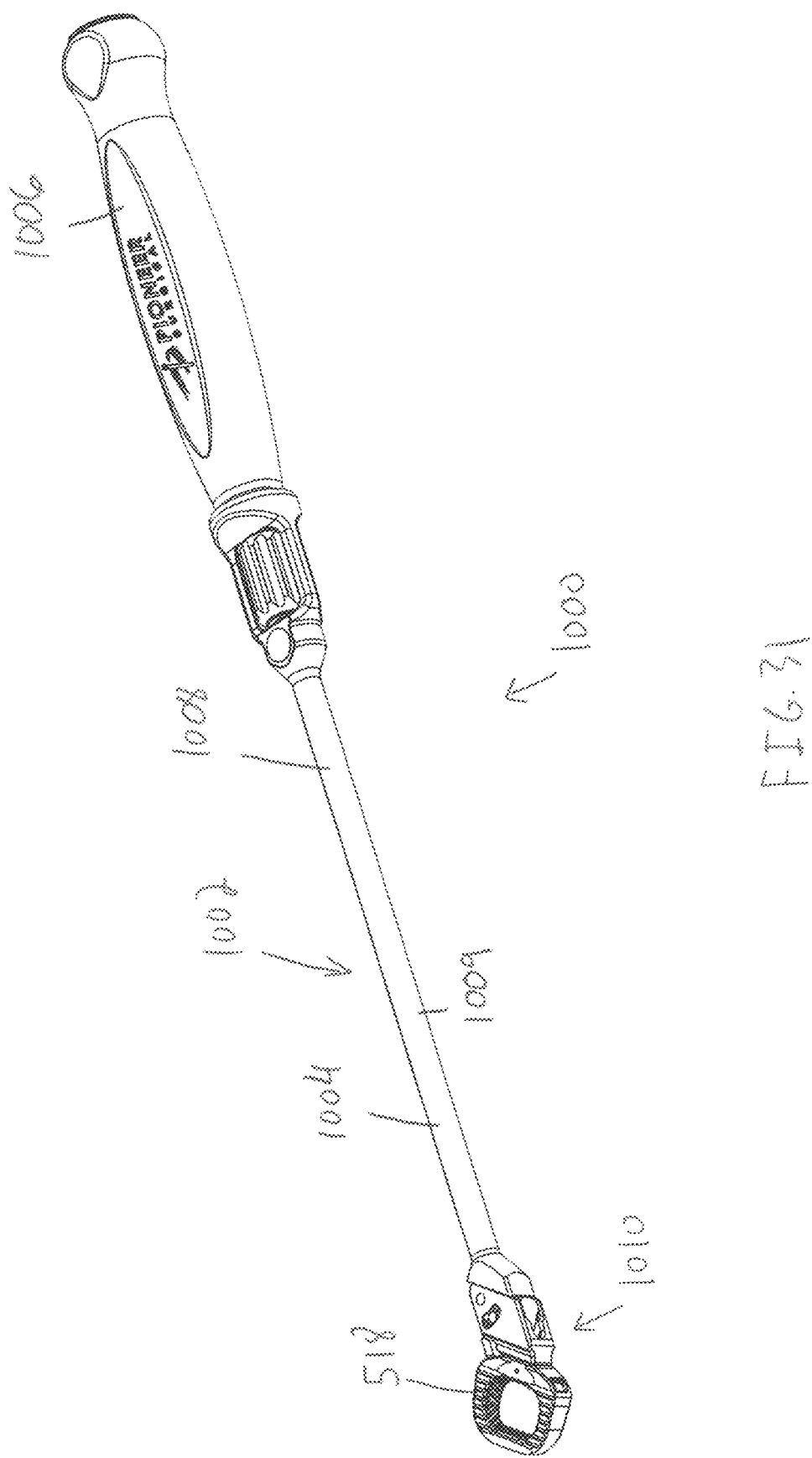
FIG. 31 is a perspective view of another inserter tool connected to an implant.

The trailing end portion 722 includes one or more pockets 920, 922, 924 for engaging the inserter tool 500. The implant 518 may be provided as a kit including the inserter tool 500 and an angled inserter tool, such as an angled inserter tool 1000 discussed below with respect below to FIG. 31. Each pocket 920, 922, 924 has an outer opening 926 that opens to an interior of the pocket 920, 922, 924 and one or more lips 750. The inserter tool 500 engages the lips 750 of the pockets 920 and 924. Conversely, the inserter tool 1000 engages the pockets 922, 924 when the inserter tool 1000 is positioned to extend to the right side of the implant 518 as shown in FIG. 31 or engages the lips 570 of the pockets 920, 922 when the inserter tool 1000 is positioned to extend toward the left side of the implant 518. The trailing end portion 722 of the implant 518 thereby permits different orientations of different tools to be utilized with a single implant 518. Regarding FIGS. 20 and 30, the walls 724, 725, 726 of the implant 518 have surfaces 950, 952, 954 with the surfaces 950, 954 being oriented at an angle 956 relative to the surface 952, such as in the range of approximately 100 degrees to approximately 175 degrees, such as approximately 160 degrees.

With reference to FIG. 31, the inserter tool 1000 includes a body 1002 including a shaft 1004 and a handle 1006. The body 1002 includes a housing 1008 having a sleeve 1009 and a distal end portion 1010. The inserter tool 1000 is similar in many respects to the inserter tool 500 discussed above such that differences between the two will be highlighted.

Figure 32:
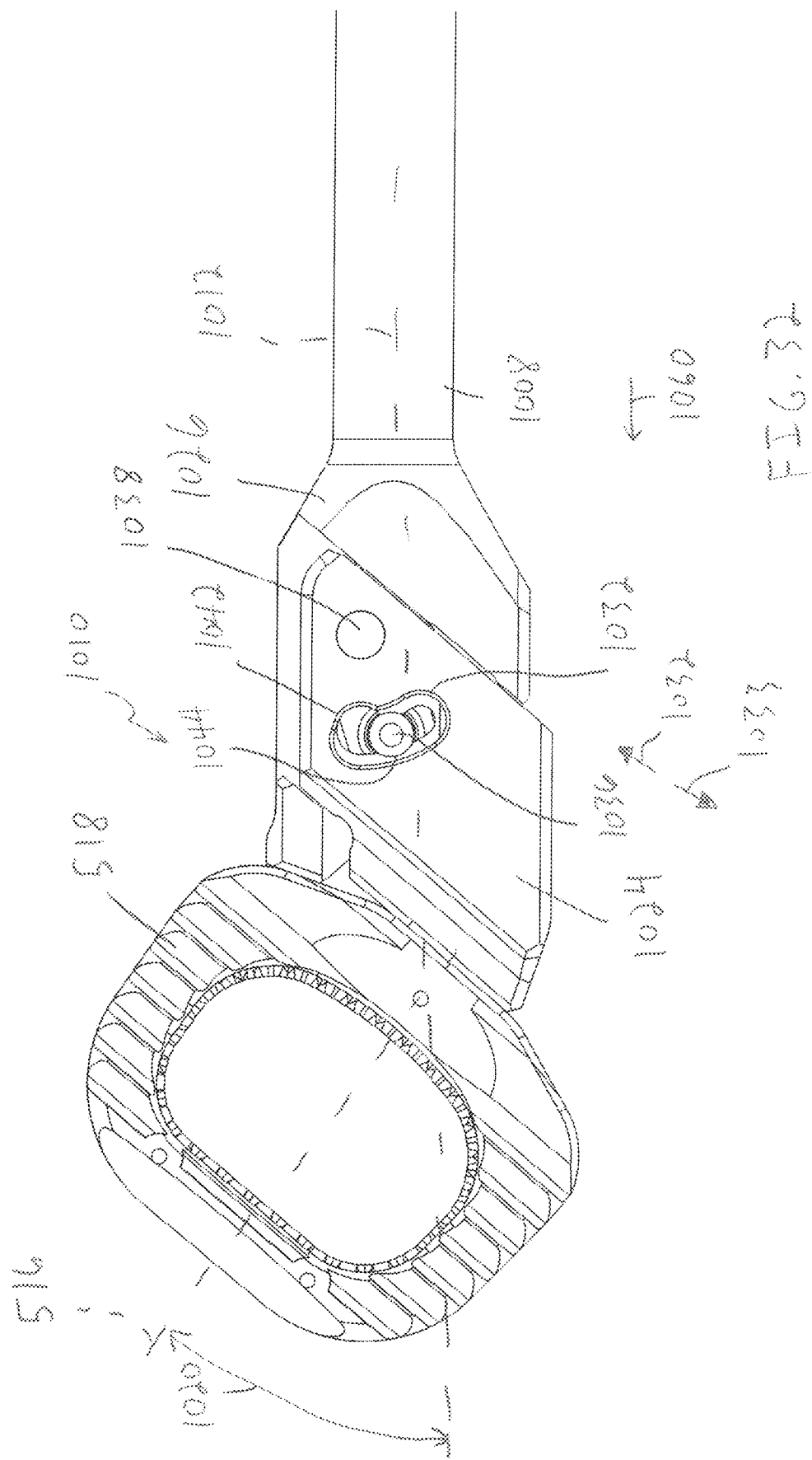
FIG. 32 is a top plan view of a distal end portion of the inserter tool of FIG. 31 showing a longitudinal axis of the implant oriented at an acute angle relative to a longitudinal axis of a shaft of the inserter tool.

With reference to FIG. 32, the inserter tool 1000 includes a longitudinal axis 1012 and the distal end portion 1010 orients implant 518 so that the longitudinal axis 516 thereof extends at an angle 1020 relative to the longitudinal axis 1012 of the inserter tool 1000. In one embodiment, the angle 1020 is in the range of, for example, approximately 5 degrees to approximately 40 degrees, such as in the range of approximately 20 degrees to approximately 40 degrees, such as in the approximately 30 degrees.

The orientation of the implant 518 relative to the shaft 1004 permits the implant 518 to be advanced into the patient and avoid tissue of the patient, such as one or more veins, that would obstruct movement of the implant 518 if the inserter tool 500 were used. As discussed above, either of the inserter tools 500, 1000 may be connected to the implant 518 depending on the anatomy of the patient. The ability to select which inserter tool 500, 1000 to utilize with the implant 518 based on the patient's anatomy provides enhanced flexibility to a surgeon.

Figure 33:
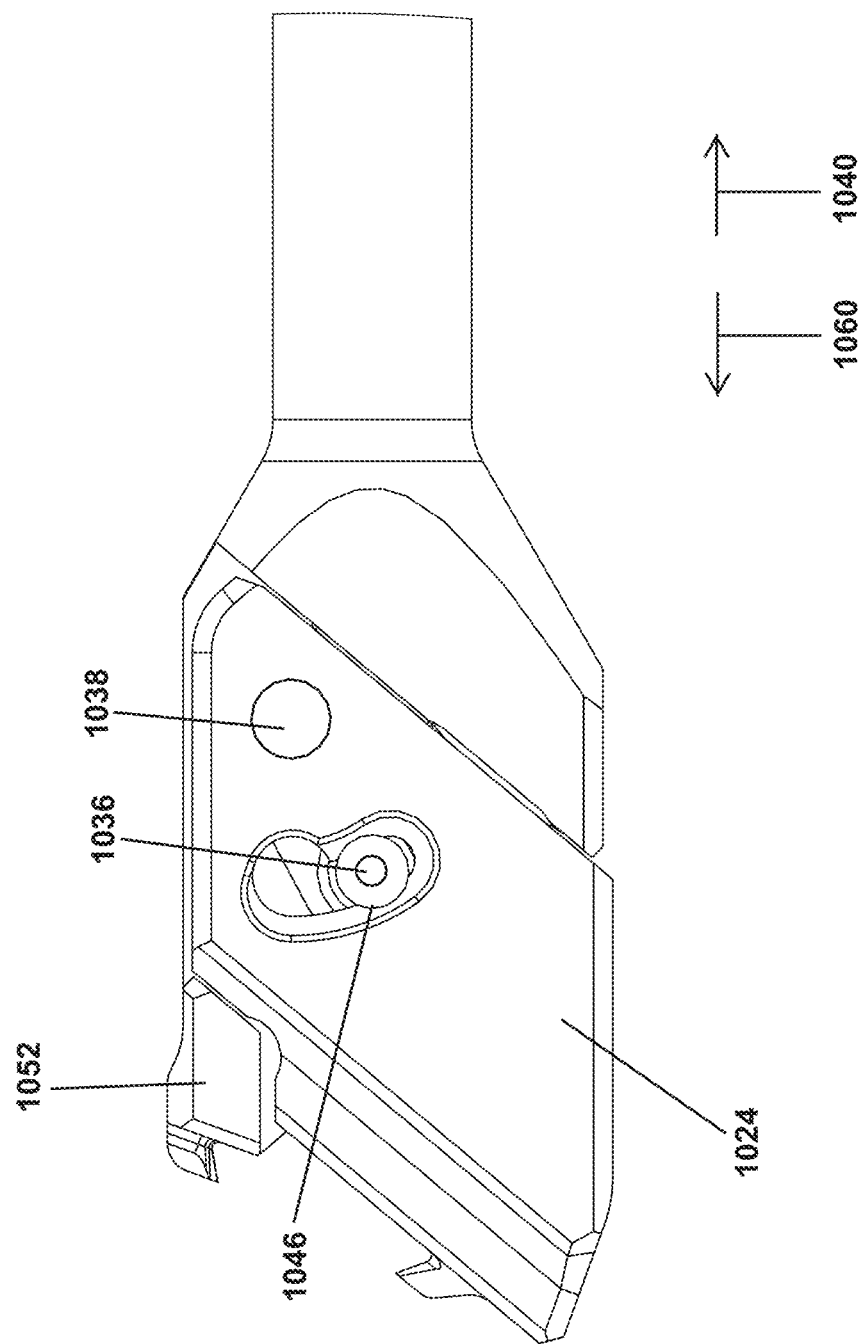
FIG. 33 is a top plan view of the distal end position of the inserter tool of FIG. 31 showing the distal end portion in a closed, implant-holding configuration.
Figure 34:
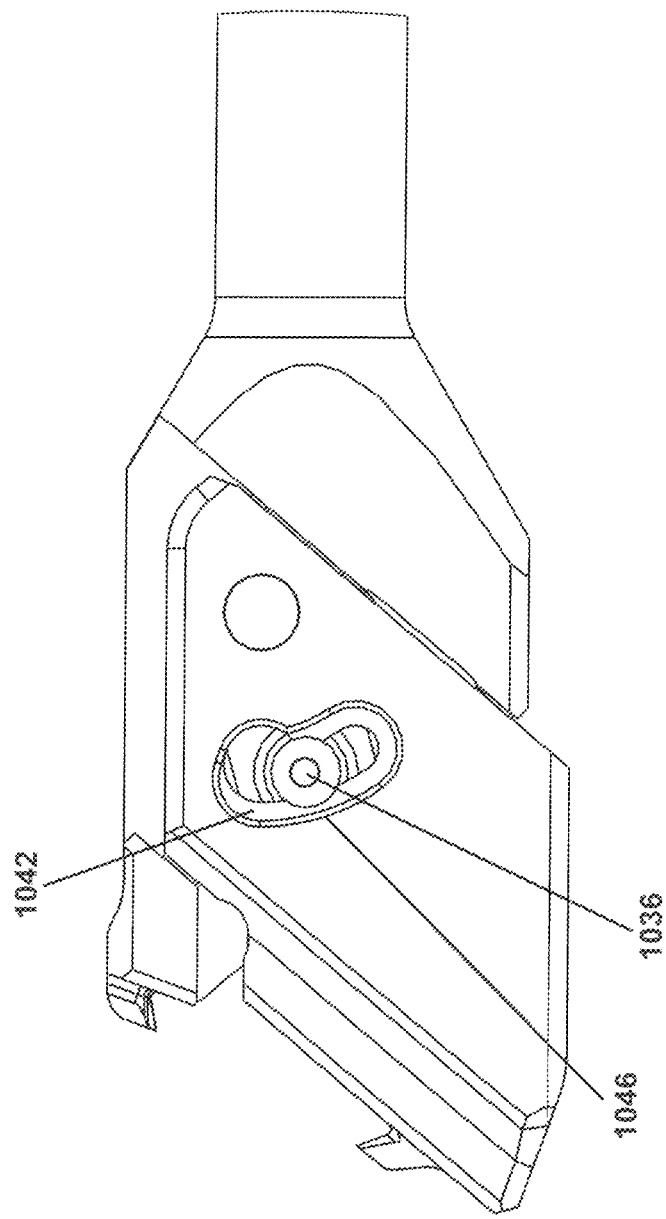
FIG. 34 is a top plan view similar to FIG. 33 showing the distal end portion of the inserter tool in an open, implant-releasing configuration.

Regarding FIGS. 32 and 33, the distal end portion 1010 includes a movable gripping body 1024, a pin 1036, and a pin 1038. FIG. 33 shows the distal end portion 1010 in a closed configuration, FIG. 34 shows the distal end portion 1010 in an open configuration, and FIG. 35 shows the distal end portion 1010 in a disassembly configuration.

Regarding FIG. 32, the gripping body 1024 is slidably connected to a guide portion 1026 of the sleeve 1009 and is shiftable in direction 1033 to an open position and in direction 1032 to a closed position. As an inner shaft of the inserter tool 1000 is shifted in a distal direction 1060 from an open position to a closed position, the pin 1036 travels along a slot 1042 from an open first position 1044 to a closed second position 1046. The pin 1036 is pivotally connected to an internal link which is in turn pivotally connected to the pin 1038. The pins 1036, 1038 and link drive the gripping body 1024 in a manner similar to the pins 558, 570 and link 564 discussed above.

Figure 35:
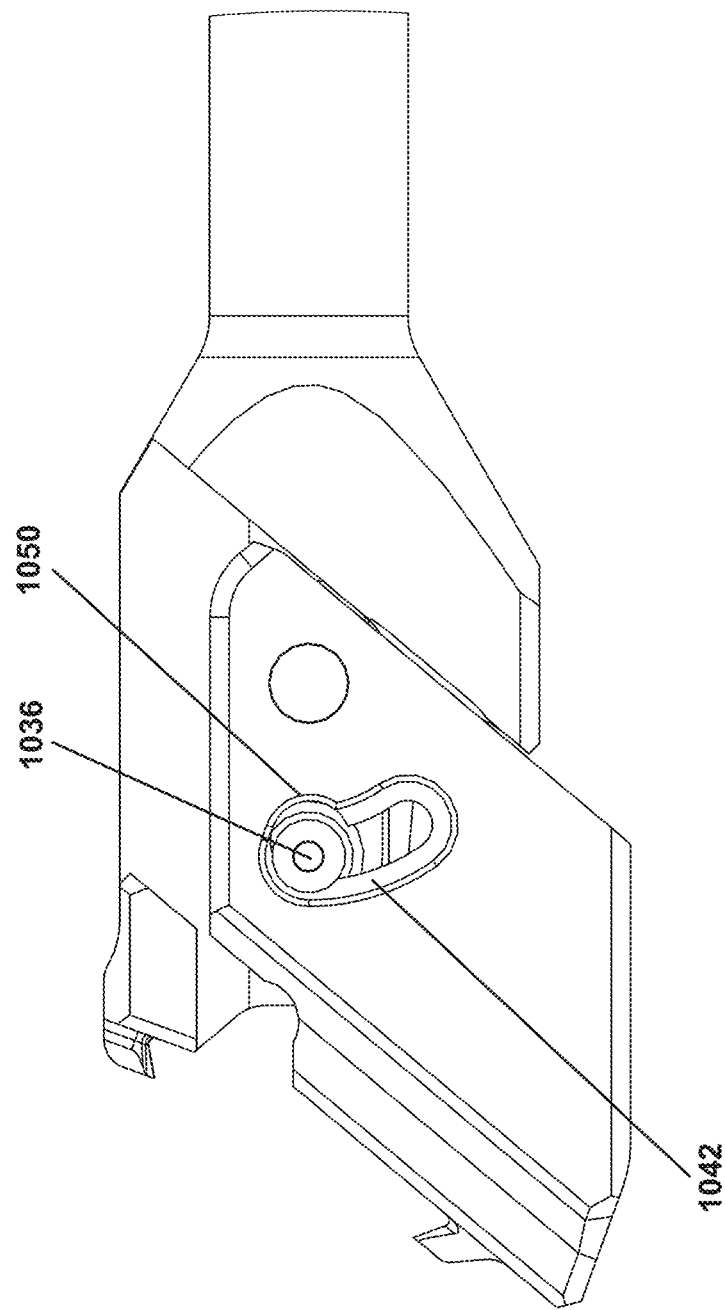
FIG. 35 is a top plan view similar to FIG. 33 showing the distal end portion of the inserter tool in a disassembly configuration.

Regarding FIG. 35, the distal end portion 1010 has a disassembly configuration wherein the pin 1036 is at an end 1050 of the slot 1042. With the distal end portion 1010 in the disassembly configuration, the gripping body 1024 and the inner shaft of the inserter tool 1000 may thereby be removed from the sleeve 1009.

While there have been illustrated and described particular embodiments of the present invention, it will be appreciated that numerous changes and modifications will occur to those skilled in the art, and it is intended for the present invention to cover all those changes and modifications which fall within the scope of the appended claims. It is intended that the phrase "at least one of" be interpreted in the disjunctive sense. For example, the phrase "at least one of A and B" is intended to encompass only A, only B, or both A and B.

What is claimed is:

1. An inserter tool for inserting an elongate intervertebral implant, the inserter tool comprising:
    a body,
    wherein a distal end portion of the body is configured to be connected to an elongate intervertebral implant to orient the elongate intervertebral implant so that an implant longitudinal axis of the intervertebral implant extends in a predetermined direction;
    wherein the body includes an elongate shaft having a shaft longitudinal axis extending obliquely to the predetermined direction;
    an offset member extending from the body; and
    an impact surface support portion of the offset member spaced apart from the body and the shaft longitudinal axis, the impact surface support portion configured to position an impact surface laterally offset from the shaft longitudinal axis and in alignment with the implant longitudinal axis to permit the impact surface to receive an impact force directed in the predetermined direction obliquely to the shaft longitudinal axis.

2. The inserter tool of claim 1 wherein the offset member extends transverse to the shaft longitudinal axis of the elongate shaft.

3. The inserter tool of claim 1 wherein the distal end portion includes a pair of gripping portions extending obliquely to the elongate shaft in the predetermined direction.

4. The inserter tool of claim 1 wherein the offset member includes a base portion connected to the elongate shaft and a free end portion spaced from the base portion that includes the impact surface support portion.

5. The inserter tool of claim 1 further comprising an actuator operatively coupled to the distal end portion and rotatable around an actuator axis extending transverse to the predetermined direction to configure the distal end portion to receive the elongate intervertebral implant, the actuator rotatable in an opposite, second direction to configure the distal end portion to retain the elongate intervertebral implant.

6. The inserter tool of claim 1 wherein the elongate shaft includes an inner shaft and an outer sleeve extending thereabout, wherein one of the inner shaft and the outer sleeve includes a pair of arms and the other of the inner shaft and the outer sleeve is configured to urge the arms together with shifting of the inner shaft relative to the outer sleeve in a locking direction.

7. The inserter tool of claim 1 wherein the offset member includes a handle portion.

8. The inserter tool of claim 1 further comprising a force imparting tool having the impact surface thereon and a releasable connection between the force imparting tool and the impact surface support portion.

9. The inserter tool of claim 8 further comprising the impact surface, wherein the impact surface is flat.

10. The inserter tool of claim 1 wherein the offset member includes a handle portion intermediate the impact surface support portion and the body.

11. An inserter tool for an intervertebral implant, the inserter tool comprising:
    an elongate offset member;
    an elongate shaft having a proximal portion connected to the elongate offset member, a distal portion opposite the proximal portion, and a longitudinal axis extending therebetween;
    the elongate offset member extending on one lateral side of the longitudinal axis of the elongate shaft along an offset member axis that extends transverse to the longitudinal axis;
    an impact surface support portion of the offset member laterally spaced from the longitudinal axis and on the one lateral side thereof, the impact surface support portion configured to position an impact surface to extend obliquely to the offset member axis and the longitudinal axis of the elongate shaft on the one lateral side of the longitudinal axis;
    a pair of arms of the elongate shaft distal portion having an unlocked configuration that permits the arms to be connected to an intervertebral implant and a locked configuration that secures the arms to the intervertebral implant; and
    a distal gripping portion of each arm extending obliquely to the longitudinal axis on an opposite lateral side of the longitudinal axis from the impact surface support portion;
    wherein the distal gripping portions of the arms are configured to orient the intervertebral implant so that the intervertebral implant extends obliquely to the longitudinal axis of the elongate shaft on the opposite lateral side of the longitudinal axis.

12. The inserter tool of claim 11 wherein the arms each include a proximal portion extending along the longitudinal axis of the elongate shaft and a bend connecting the distal gripping portion to the proximal portion of the arm so that the distal gripping portion projects transversely from the proximal portion of the respective arm.

13. The inserter tool of claim 11 wherein the elongate shaft comprises an outer sleeve and an inner shaft, wherein one of the outer sleeve and the inner shaft includes the pair of arms and the other of the outer shaft and the inner sleeve includes a surface configured to engage the arms and urge the arms together to the locked configuration with shifting of the outer sleeve and inner shaft relative to each other in a locking direction.

14. The inserter tool of claim 13 wherein the inner shaft includes the pair of arms and a resilient fork portion that biases the arms apart to the unlocked configuration with shifting of the outer sleeve and inner shaft relative to each other in an unlocking direction.

15. The inserter tool of claim 11 further comprising an actuator operatively coupled to the arms and rotatable in a first direction to shift the arms to the locked configuration, the actuator rotatable in an opposite, second direction to shift the arms to the unlocked configuration.

16. The inserter tool of claim 15 wherein the elongate shaft comprises an outer housing including a sleeve portion and an inner shaft extending in the sleeve portion, the actuator rotatably mounted to the outer housing and threadingly engaged with the inner shaft.

17. An inserter tool for an intervertebral implant, the inserter tool comprising:
    an elongate shaft comprising an outer sleeve and an inner shaft extending in the outer sleeve;
    a pair of arms of the elongate shaft, the arms resiliently biased apart and configured to engage an intervertebral implant;
    a first plurality of cam surfaces of the outer sleeve and the inner shaft;
    a proximal actuator operatively coupled to the outer sleeve and the inner shaft and configured to shift the inner shaft and the outer sleeve relative to one another in a locking direction to engage the first plurality of cam surfaces that urge the arms together against the resilient bias of the arms and cause the arms to clamp an implant portion of the intervertebral implant therebetween, the actuator further configured to shift the inner shaft and the outer sleeve relative to one another in an opposite, unlocking direction which permits the resilient bias of the arms to separate the arms and release the implant portion; and
    a second plurality of cam surfaces of the outer sleeve and the inner shaft distinct from the first plurality of cam surfaces, the second plurality of cam surfaces configured to engage and separate the arms with shifting of the inner shaft and the outer sleeve relative to each other in the unlocking direction upon the resilient bias of the arms being insufficient to separate the arms and release the implant portion.

18. The inserter tool of claim 17 wherein the outer sleeve further includes one of grooves and projections sized to extend in grooves and the inner shaft includes the other of the grooves and the projections, wherein the grooves and the projections include the second plurality of cam surfaces thereon.

19. The inserter tool of claim 17 wherein the elongate shaft has a longitudinal axis and the second plurality of cam surfaces include a pair of inclined surfaces extending in opposite directions transverse to the longitudinal axis of the elongate shaft.

20. The inserter tool of claim 17 wherein the outer sleeve and the inner shaft further include stop surfaces that abut and limit shifting of the inner shaft and outer sleeve relative to one another in the locking direction.

21. The inserter tool of claim 20 further comprising an impact surface connected to the outer sleeve and wherein the outer sleeve transfers impacts from the impact surface to the inner shaft via the abutting stop surfaces.

22. The inserter tool of claim 17 wherein the proximal actuator includes a knob threadingly engaged with the inner shaft.

23. The inserter tool of claim 17 wherein the elongate shaft has a longitudinal axis; and
    wherein the second plurality of cam surfaces are closer to the longitudinal axis than the first plurality of cam surfaces.

24. The inserter tool of claim 17 wherein the outer sleeve includes a pair of channels and the inner shaft includes bosses each sized and configured to move in a respective one of the pair of channels; and wherein the pair of channels and the bosses include the second plurality of cam surfaces.

25. An inserter tool for an intervertebral implant, the inserter tool comprising:
    an offset member;
    an elongate shaft having a proximal portion connected to the offset member, a distal portion opposite the proximal portion, and a longitudinal axis extending therebetween;
    an impact surface support portion of the offset member laterally spaced from the longitudinal axis of the elongate shaft and on one lateral side thereof;
    a pair of arms of the elongate shaft distal portion having an unlocked configuration that permits the arms to be connected to an intervertebral implant and a locked configuration that secures the arms to the intervertebral implant;
    a distal gripping portion of each arm extending obliquely with respect to the longitudinal axis of the elongate shaft on an opposite lateral side of the longitudinal axis from the impact surface support portion;
    wherein the distal gripping portions of the arms are configured to orient the intervertebral implant so that the intervertebral implant extends obliquely to the longitudinal axis of the elongate shaft on the opposite lateral side of the longitudinal axis; and
    wherein the elongate shaft includes a housing having a connecting portion with a non-circular cross section taken perpendicular to the longitudinal axis of the elongate shaft sized to extend through a non-circular opening of the offset member and matingly fit therewith.

26. The inserter tool of claim 25 wherein the housing further includes a flange distal of the connecting portion and a support portion proximal of the connecting portion; and
    a locking member configured to engage the support portion of the housing and clamp the offset member between the flange and the locking member.

27. An inserter tool for inserting an elongate intervertebral implant, the inserter tool comprising:
    a body,
    wherein a distal end portion of the body is configured to be connected to an elongate intervertebral implant to orient the elongate intervertebral implant so that an implant longitudinal axis of the intervertebral implant extends in a predetermined direction;
    an offset member extending from the body;
    an impact surface support portion of the offset member spaced apart from the body and configured to position an impact surface in alignment with the longitudinal axis of the elongated intervertebral implant to permit the impact surface to receive an impact force directed in the predetermined direction;
    wherein the body includes an elongate shaft having a longitudinal axis extending transverse to the predetermined direction and wherein the offset member extends transverse to the longitudinal axis of the elongate shaft; and
    wherein the offset member is elongated along an offset member axis extending perpendicular to the elongate shaft longitudinal axis and the impact surface support portion is configured to position the impact surface to extend obliquely to the offset member axis.

28. An inserter tool for an intervertebral implant, the inserter tool comprising:
    an offset member;

an elongate shaft having a proximal portion connected to the offset member, a distal portion opposite the proximal portion, and a longitudinal axis extending therebetween;

an impact surface support portion of the offset member laterally spaced from the longitudinal axis of the elongate shaft and on one lateral side thereof;

a pair of arms of the elongate shaft distal portion having an unlocked configuration that permits the arms to be connected to an intervertebral implant and a locked configuration that secures the arms to the intervertebral implant;

a distal gripping portion of each arm extending obliquely with respect to the longitudinal axis of the elongate shaft on an opposite lateral side of the longitudinal axis from the impact surface support portion;

wherein the distal gripping portions of the arms are configured to orient the intervertebral implant so that the intervertebral implant extends obliquely to the longitudinal axis of the elongate shaft on the opposite lateral side of the longitudinal axis;

wherein the elongate shaft comprises an outer sleeve and an inner shaft that are movable relative to each other; and wherein the inserter tool further comprises a detent member configured to contact at least one of the outer sleeve and the inner shaft and limit movement of the at least one of the outer sleeve and the inner shaft; and a biasing member urging the detent member into contact with the at least one of the outer sleeve and the inner shaft.

* * * * *